US012773109B2

(12) United States Patent
Munoz et al.

(10) Patent No.: US 12,773,109 B2
(45) Date of Patent: Oct. 27, 2026

(54) SINGLE-USE VAGINAL SPECULUM SYSTEMS AND METHODS

(71) Applicant: MY VILLAGE INNOVATIONS INC, Encinitas, CA (US)

(72) Inventors: Andrea Munoz, Encinitas, CA (US); Alfonso Munoz, Encinitas, CA (US); David Morelock, Escondido, CA (US); Brian Bowman, Carlsbad, CA (US); Maisha Zaman, Carlsbad, CA (US); Benjamin Arnold, San Diego, CA (US)

(73) Assignee: MY VILLAGE INNOVATIONS INC, Encinitas, CA (US)

( * ) Notice: Subject to any disclaimer, the term of this patent is extended or adjusted under 35 U.S.C. 154(b) by 0 days.

(21) Appl. No.: 19/020,502

(22) Filed: Jan. 14, 2025

(65) Prior Publication Data

US 2025/0143560 A1 May 8, 2025

Related U.S. Application Data

(63) Continuation-in-part of application No. 17/226,802, filed on Apr. 9, 2021, now Pat. No. 12,232,708.

(60) Provisional application No. 63/717,265, filed on Nov. 6, 2024, provisional application No. 63/101,187, filed on Sep. 25, 2024, provisional application No. 62/972,952, filed on Feb. 11, 2020.

(51) Int. Cl.
*A61B 1/32* (2006.01)
*A61B 1/303* (2006.01)

(52) U.S. Cl.
CPC ................ *A61B 1/32* (2013.01); *A61B 1/303* (2013.01)

(58) Field of Classification Search
None
See application file for complete search history.

(56) References Cited

U.S. PATENT DOCUMENTS

| | | | | |
|---|---|---|---|---|
| 196,600 A * | 10/1877 | Shiland | ............. | A61B 17/0218 600/201 |
| 5,505,690 A | 4/1996 | Patton et al. | | |
| 5,509,893 A * | 4/1996 | Pracas | ...................... | A61B 1/32 600/184 |

(Continued)

FOREIGN PATENT DOCUMENTS

| | | |
|---|---|---|
| CN | 208822739 | 5/2019 |
| CN | 221154177 | 6/2024 |

(Continued)

*Primary Examiner* — Eduardo C Robert
*Assistant Examiner* — Anna V. Little
(74) *Attorney, Agent, or Firm* — PIERSON FERDINAND LLP; Keats Quinalty

(57) ABSTRACT

Disclosed are speculum embodiments and related methods to comfortably dilate a woman's vaginal canal during a pelvic exam. In one aspect, a flute having retractable rods and foldable rings are provided. The flute is configured to transition between an expanded state where the proximal and distal foldable rings are in an unfolded orientation and a collapsed state where the proximal and distal foldable rings are in a folded orientation. A handle maintains the flute in the collapsed state and, in at least one embodiment, a ring collar is provided and configured to engage the flute when the flute is in the expanded state. A light source can be provided in the flute or ring collar.

22 Claims, 35 Drawing Sheets

(56) References Cited

U.S. PATENT DOCUMENTS

| | | | | |
|---|---|---|---|---|
| 5,916,151 | A * | 6/1999 | Charters | A61B 1/32 606/198 |
| 6,280,379 | B1 * | 8/2001 | Resnick | A61B 1/32 600/220 |
| 6,527,710 | B1 * | 3/2003 | Davidson | A61B 17/42 600/222 |
| 8,460,187 | B2 | 6/2013 | Bouquet | |
| 11,712,547 | B2 | 8/2023 | Juravic | |
| 11,931,012 | B2 | 3/2024 | Bouquet | |
| 2008/0039865 | A1 * | 2/2008 | Shaher | A61B 17/0206 606/119 |
| 2008/0146886 | A1 * | 6/2008 | Lucas | A61B 1/303 600/220 |
| 2010/0016674 | A1 * | 1/2010 | Mills | A61B 1/32 600/207 |
| 2010/0036312 | A1 * | 2/2010 | Krolik | A61M 25/0068 606/159 |
| 2012/0316399 | A1 * | 12/2012 | Muzzammel | A61B 1/32 600/221 |
| 2018/0344144 | A1 * | 12/2018 | Bouquet | A61B 1/0669 |
| 2019/0000310 | A1 | 1/2019 | Prendiville et al. | |
| 2021/0315450 | A1 * | 10/2021 | Kort | A61B 1/015 |
| 2023/0337903 | A1 | 10/2023 | Wolny et al. | |

FOREIGN PATENT DOCUMENTS

| | | | |
|---|---|---|---|
| CN | 118452807 | 8/2024 | |
| CN | 118512147 | 8/2024 | |
| GB | 2271283 | 4/1994 | |
| GB | 2335602 | 9/1999 | |
| WO | WO-2017117308 A2 * | 7/2017 | A61B 1/303 |
| WO | 2020096666 | 5/2020 | |

* cited by examiner

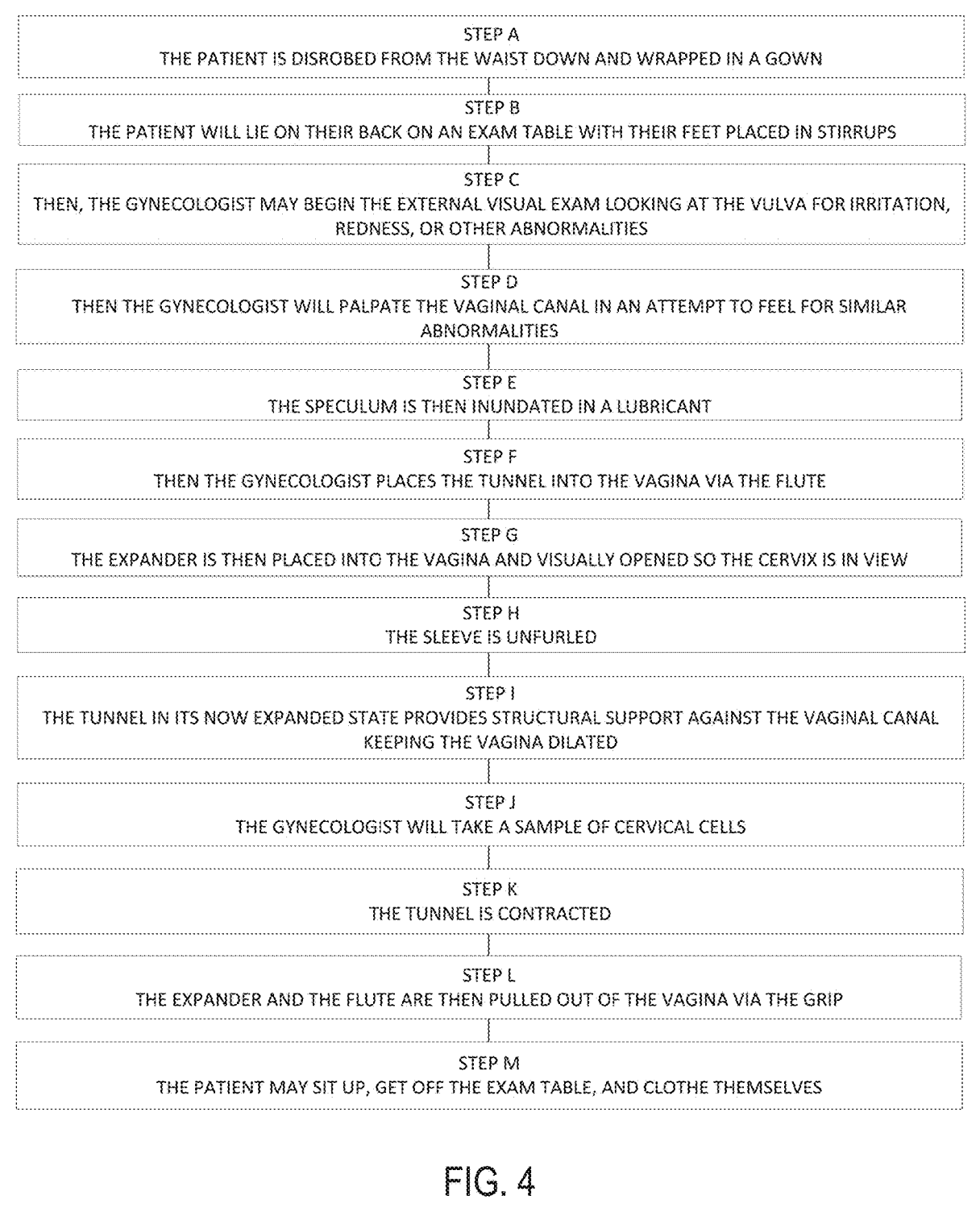

STEP A
THE PATIENT IS DISROBED FROM THE WAIST DOWN AND WRAPPED IN A GOWN

STEP B
THE PATIENT WILL LIE ON THEIR BACK ON AN EXAM TABLE WITH THEIR FEET PLACED IN STIRRUPS

STEP C
THEN, THE GYNECOLOGIST MAY BEGIN THE EXTERNAL VISUAL EXAM LOOKING AT THE VULVA FOR IRRITATION, REDNESS, OR OTHER ABNORMALITIES

STEP D
THEN THE GYNECOLOGIST WILL PALPATE THE VAGINAL CANAL IN AN ATTEMPT TO FEEL FOR SIMILAR ABNORMALITIES

STEP E
THE SPECULUM IS THEN INUNDATED IN A LUBRICANT

STEP F
THEN THE GYNECOLOGIST PLACES THE TUNNEL INTO THE VAGINA VIA THE FLUTE

STEP G
THE EXPANDER IS THEN PLACED INTO THE VAGINA AND VISUALLY OPENED SO THE CERVIX IS IN VIEW

STEP H
THE SLEEVE IS UNFURLED

STEP I
THE TUNNEL IN ITS NOW EXPANDED STATE PROVIDES STRUCTURAL SUPPORT AGAINST THE VAGINAL CANAL KEEPING THE VAGINA DILATED

STEP J
THE GYNECOLOGIST WILL TAKE A SAMPLE OF CERVICAL CELLS

STEP K
THE TUNNEL IS CONTRACTED

STEP L
THE EXPANDER AND THE FLUTE ARE THEN PULLED OUT OF THE VAGINA VIA THE GRIP

STEP M
THE PATIENT MAY SIT UP, GET OFF THE EXAM TABLE, AND CLOTHE THEMSELVES

FIG. 4

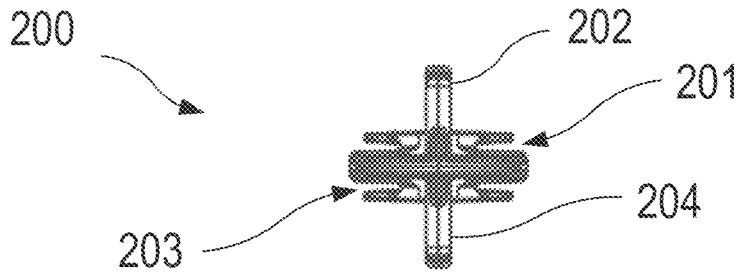
FIG. 16A
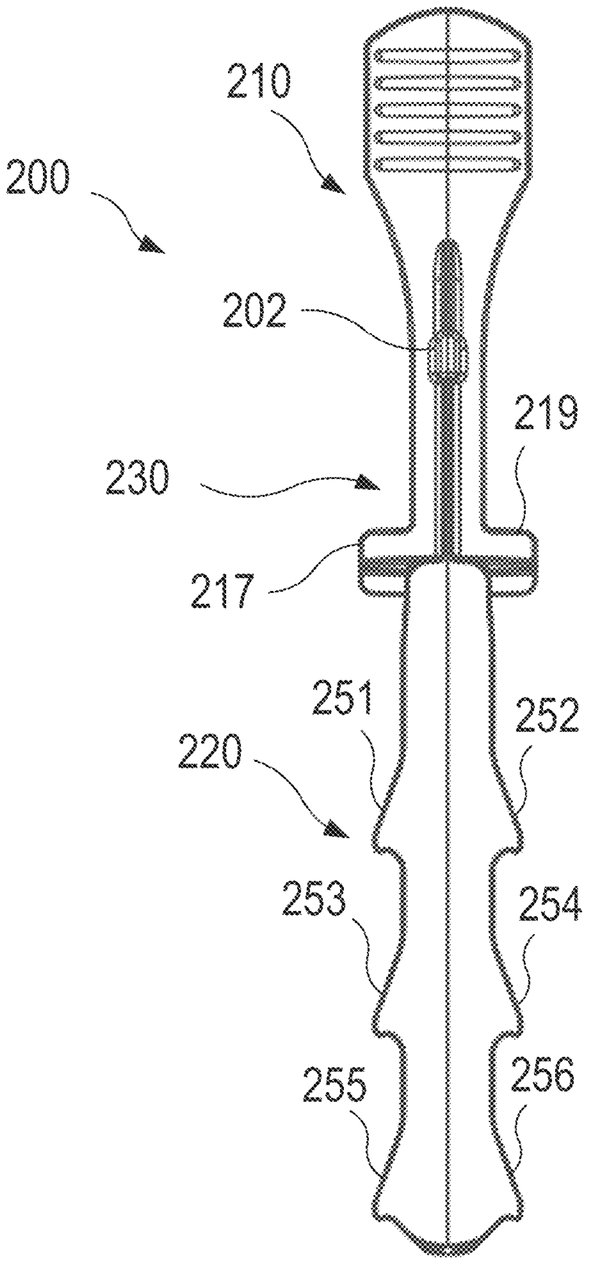
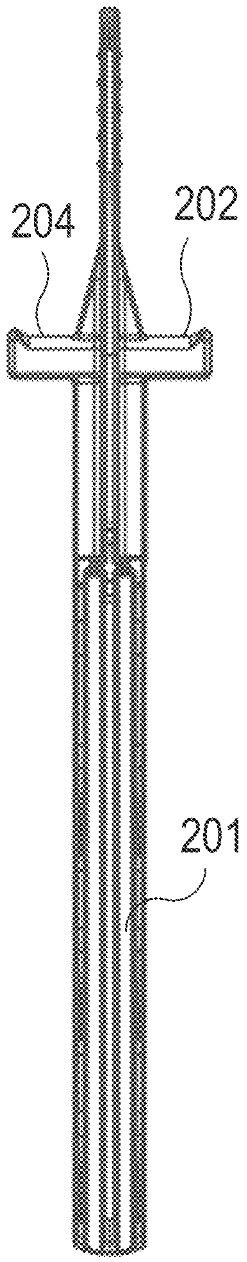
FIG. 16B FIG. 16C

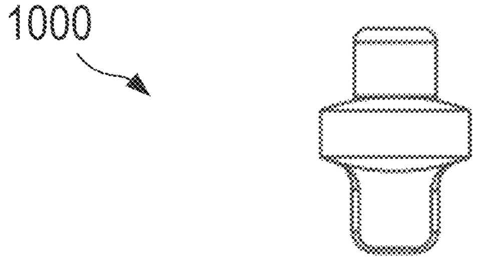
FIG. 17A
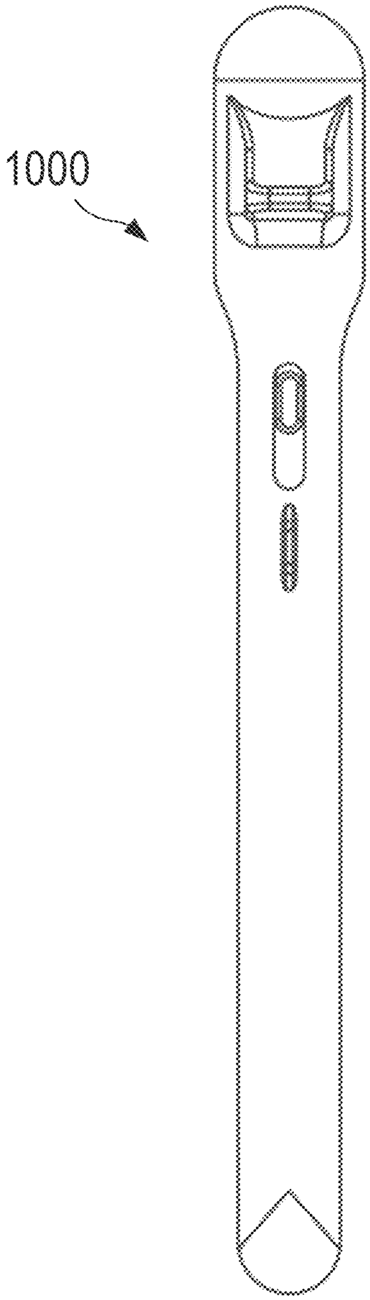
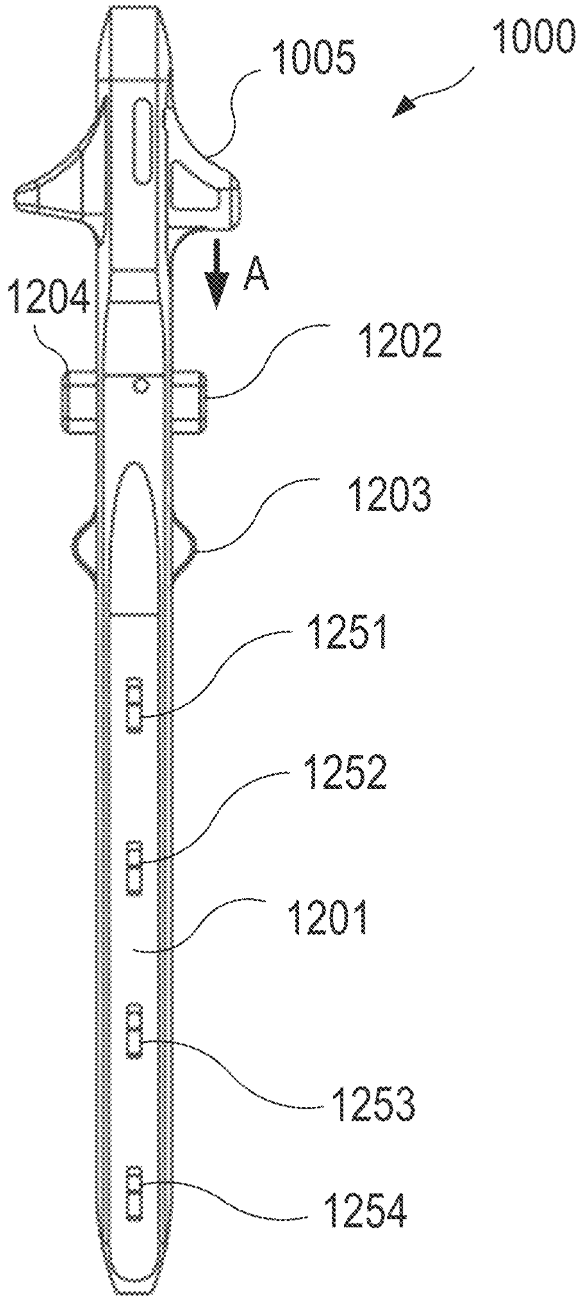
FIG. 17B FIG. 17C

SINGLE-USE VAGINAL SPECULUM SYSTEMS AND METHODS

CROSS-REFERENCE TO RELATED APPLICATIONS

This application claims the benefit of U.S. Provisional Application No. 63/717,265, filed Nov. 6, 2024, and U.S. Provisional Application 63/101,187, which was originally filed Sep. 25, 2024 as U.S. application Ser. No. 18/896,710 before being converted to provisional, and is a continuation-in-part of U.S. patent application Ser. No. 17/226,802, filed Apr. 9, 2021, which claims the benefit of U.S. Provisional Application 62/972,952, filed Feb. 11, 2020, each of which are incorporated herein by reference in their entirety as if repeated herein.

BACKGROUND

Embodiments of the present disclosure relate generally to medical devices, and in particular instances, to gynecological medical devices and methods.

The female anatomy is comprised of many unique reproductive organs. Specifically, the internal reproductive organs are the vagina, cervix, uterus, fallopian tubes, and ovaries. These organs have many functions. They are used for childbirth, sexual intercourse, procreation, and menstruation. To remain functional, these organs must remain healthy. Reproductive health has its own challenges. Women must take special steps to keep their reproductive systems healthy, as there are many medical complications which can lead to the downfall of a woman's reproductive health.

Like any other system in the human body, the health of each organ of the female reproductive system is important for the entire system to properly function. There are a wide array of common reproductive health concerns for women, some of which being endometriosis, fibroids, cancer, ovarian cysts, and sexually transmitted diseases. A woman aged 21 and older should have annual physical exams, routine screenings and be evaluated if she believes she is suffering from complications related to her reproductive health. If these health concerns are not dealt with in a timely manner, they may cause pain, infertility, or death.

Many steps must be taken to maintain a healthy reproductive system. An important step in maintaining a healthy reproductive system in a woman is having regular visits to a gynecologist, a type of doctor whose practice is focused on dealing with the health of the female reproductive system. If a woman believes she is having issues with her reproductive system it is important for a medical professional to actually evaluate these organs. This process is called a pelvic exam.

A pelvic exam is a physical exam of the internal and external female pelvic organs. It is used for evaluation of the female productive organs and urinary tract. It is recommended that women 21 years old and older have an annual physical examination which includes a pelvic exam. Symptoms such as pain, heavy or abnormal bleeding, discharge, or incontinence are indications that a pelvic exam is necessary. Annual screening is important because some diseases or infections of the reproductive system may be asymptomatic. A pelvic exam may also be necessary if a woman has been sexually assaulted or to assess a woman's anatomy in preparation for a medical procedure.

The examination is performed in three steps. The first step is an external visual examination, next step is an internal visual examination using a speculum, which may include a pap smear, and the last step is an internal palpation examination. The external visual examination involves the gynecologist simply looking at the external reproductive organs with the naked eye. The internal visual exam with a speculum allows a gynecologist to view the vaginal walls and cervix. The speculum is placed inside the vaginal canal and expanded. This dilation puts the vagina and cervix in view. During this step a medical professional may also conduct a pap smear. During each step the gynecologist is looking for abnormalities such as lesions, ulcerations, discharge, or unusual growths. Internal palpation involves a medical professional palpating from inside the vagina and outside the lower abdomen. Specifically, the gynecologist is checking the condition of the uterus and ovaries.

The speculum is a necessary tool in a pelvic exam which allows for visualization of the cervix and vagina. The average length of a vaginal canal is three to four inches long. The vaginal tissue has elastic qualities which make the vagina easily collapsible, which makes the cervix and vagina very hard to view. The speculum is a tool used to retract the vaginal walls. The speculum does this by being inserted into the vagina then expanding. This retraction and expansion puts the vaginal walls and cervix in view for a medical professional.

There are many different speculum designs. They have a duck bill like shape with similar dimensions to the vagina. Speculums can have either one, two, or three blades for retraction. Speculums have different sizes for different sized women of different ages. Such speculums are made out of plastic or metal. Metal speculums are reusable and must be sterilized, while plastic speculums are disposable. Some speculums are outfitted with a light source.

The most common type of speculum is a bivalve speculum (shown in FIG. 5). The bivalve speculum has a handle, a screw, and two blades. During the exam, a medical professional starts by inserting the blades into the vagina. Then the handle is squeezed. This causes the duckbill like blades to be pulled part. Once the blades are a necessary distance apart, the screw is engaged to lock the speculum in in an open position. Once the examination is over the screw is disengaged to unlock the blades. The blades are then closed and the tool removed from the vagina.

Proper practices during the exam are an absolute necessity for patients to maintain their dignity and modesty. The gynecologist must obtain informed consent from the patient before the exam begins. Each part of the exam must be explained by the gynecologist to the patient before it is done. The patient is to be undressed only the minimum amount of time necessary to conduct the exam. These exams are conducted on sterile medical examination tables, preferably with foot supports. The patient is to be undressed from the waist down and covered with a sheet. Many exams include the presence of a chaperone, especially in the event that the medical provider is a male.

A pelvic exam may feel intrusive and uncomfortable for some women. A woman's vagina is considered a private place, one which may be reserved for intimacy. It is a part of her body, and hers alone. She has the right to say what does or does not happen there. Pelvic exams may feel intrusive and invasive. They may involve an unfamiliar person entering and touching a private area of one's body with inorganic tools. These exams involve cold metal or plastic instruments. They involve invasive poking and prodding of sensitive areas. The exams are uncomfortable, unfamiliar, awkward, and perhaps violating. Inherently, these exams elicit stress and anxiety in women. Although these exams are uncomfortable, they are necessary. Thus, a need exists for a tool which can be used to retract the vagina during pelvic exams without causing women a slew of negative emotions.

Current devices enable health providers to provide beneficial examinations to patients. Yet still further improvements in speculum systems and methods are desired. Embodiments of the present disclosure provide solutions to at least some of these outstanding needs.

BRIEF SUMMARY

An object of this specification is to disclose a tool that comfortably dilates a woman's vagina for a pelvic exam.

It is yet another object of this specification to disclose a tool that allows for viewing of the vagina and the cervix for medical evaluation and treatments. In one embodiment, the above objectives are met by disclosing a vaginal speculum used to maintain vaginal dilation comprising: a flute; and an expander. That apparatus could further include wherein said flute features a tunnel at a proximal end. That apparatus could further include wherein the tunnel comprises a sleeve which is a hollow cylinder made out of a film and wherein the film uses a lip and a plurality of spines to maintain its structure. In another embodiment, the above objectives are met by disclosing a tilting hoop vaginal speculum used to maintain vaginal dilation comprising: handle, a guide rod, at least one tilting hoop rotatably attached to the guide rod, and a driving mechanism disposed in the handle for tilting the hoop between a retracted configuration and a deployed configuration. That apparatus could further include wherein said driving mechanism is a rotary dial that is coupled to a foot of the hoop via two pistons that operate to push or pull the foot so that the hoop rotates between the two stated configurations.

Disclosed may also be a related method of dilating a vagina during a pelvic exam comprising: placing a speculum in a vagina via a flute or guide rod, expanding a tunnel via a thread or rotating a hoop disposed on the guide rod via a rotary dial until the hoop is in a deployed configuration, contracting the tunnel via the expander or rotating the hoop via the dial until the hoop is in a retracted configuration, and removing the speculum via the flute or else via the guide rod.

In one aspect, embodiments of the present disclosure encompass vaginal speculums and related methods that can be used to maintain vaginal dilation. Exemplary speculums can include a flute and an expander. A flute can be defined by a circular lip on a tip of a support rod and circular rings distributed along the length of the support rod. The circular lip may be foldable. An expander can be defined by a rod, and can operate to unfold a foldable circular lip, for expanding the rings to dilate the vaginal walls and for supporting the foldable circular lip of the flute in an expanded configuration. Circular rings can be distributed along a length of the expander so that the cervix can be viewed through and between the rings and the foldable circular lip in the expanded configuration. In some cases, the foldable circular lip and the circular rings are coaxial relative to each other when the foldable circular lip is folded and when the foldable circular lip is unfolded. In some cases, a flute features a tunnel (e.g. at a proximal end thereof). In some cases, a tunnel includes a sleeve which is a hollow cylinder made out of a film. In some cases, the film uses a lip (e.g. at the tip of the control rod) and a plurality of spines (e.g. of the rings) to maintain its structure. In some cases, spines can be in the shape of rings. In some cases, the entire speculum or a portion thereof can be lined with silicone. In some cases, a catch can be attached to the proximal end of the expander.

In another aspect, embodiments of the present disclosure encompass a tilting hoop vaginal speculum configured to maintain vaginal dilation. A tilting hoop vaginal speculum can include a handle, a guide rod, at least one tilting hoop rotatably attached to the guide rod, and a driving mechanism disposed in the handle for tilting the hoop between a retracted configuration and a deployed configuration. In some cases, the driving mechanism is a rotary dial that is coupled to a foot of the hoop via two pistons that operate to push or pull the foot so that the hoop rotates between the two stated configurations.

In another aspect, embodiments of the present disclosure encompass methods of dilating a vagina (e.g. for viewing a cervix) during a pelvic exam (e.g. by a gynecologist). Exemplary methods include placing a speculum in a vagina via a guide rod, expanding a tunnel via an expander or rotating (unfolding) a hoop disposed on the tip of the guide rod via a rotary dial until the hoop is in a deployed configuration. In some cases, this can be performed such that a grip of the guide rod is circumferentially spaced relative to a grip of the expander. In some cases, this can be performed such that circular spines are distributed along a length of the expander and along a length of the flute. In some cases, this can be performed such that circular spines are tangential to the expander. Methods can include viewing the cervix while the full-circular spines are supported by the expander and the guide rod and while the compressive force of the vaginal wall of the vagina are being counteracted, so that the cervix may be viewed via looking between the grips (e.g. of the expander and guide rod) and through at least one of the fill circular spines and an unfolded hoop. In some cases, methods can involve supporting the full-circular spines via the expander and the guide rod to counteract a compressive force of a vaginal wall of the vagina. Methods can also include contracting the tunnel via the expander or rotating the hoop via rotating the dial until the hoop is in a retracted configuration. In some cases, the hoop and the circular spines are coaxial relative to each other when the foldable hoop is folded and when the hoop is unfolded. Methods can also include removing the speculum via the flute or else via the guide rod. In some cases, an expander can attach to a lip of a tunnel via a catch during contraction. In some cases, a tunnel of the speculum can be illuminated with an internal light. In some cases, a tunnel can be given structural support by a flute, guide rod, expander, and/or a plurality spines (e.g. circular spines). In some cases, a tunnel can be fixed to a guide rod. In some cases, a dial can include detents. In some cases, the hoops can be illuminated with a guide light. In some cases, the hoops can be given structural support by guide rod. In some cases, a tunnel can be defined by the hoops. In some cases, a speculum can include a string that can operate to pull a flute along the length of the support rods after the rings (and/or foldable circular lip) have achieved an expanded configuration.

In another aspect, embodiments of the present disclosure encompass systems and methods for dilating a vagina of a patient during a pelvic exam. Exemplary systems may include a flute, a handle, and a ring collar. In some cases, a flute can include a first retracting rod, a second retracting rod, a first nesting rod, a second nesting rod, a proximal foldable ring, and a distal foldable ring. In some cases, a handle can include a first proximal coupling mechanism configured to releasably couple with the first retracting rod, a second proximal coupling mechanism configured to releasably couple with the first retracting rod, a first groove configured to at least partially receive the first nesting rod, a second groove configured to at least partially receive the second nesting rod, and a first gripping mechanism and a second gripping mechanism operable to engage the flute when the proximal and distal foldable rings are in a folded orientation. In some cases, the flute is configured to transition between an expanded state where the proximal and distal foldable rings are in an unfolded orientation and a collapsed state where the proximal and distal foldable rings are in a folded orientation. In some cases, the handle is configured to maintain the flute in the collapsed state when the first proximal coupling mechanism is coupled with the first retracting rod, the second proximal coupling mechanism is coupled with the second retracting rod, and the first and second gripping mechanisms are engaged with the flute. In some cases, the ring collar is configured to engage the flute when the flute is in the expanded state. According to some embodiments, the first proximal coupling mechanism includes a first proximal extrusion, the second proximal coupling mechanism includes a second proximal extrusion, the first retracting rod includes a first slot configured to engage the first proximal extrusion, and the second retracting rod includes a second slot configured to engage the second proximal extrusion. In some embodiments, the first gripping mechanism includes a first external gripping mechanism having a first distal barb configured to engage a first narrow portion of the distal foldable ring, a second distal barb configured to engage a second narrow portion of the distal foldable ring, a first proximal barb configured to engage a first narrow portion of the proximal foldable ring, and a second proximal barb configured to engage a second narrow portion of the proximal foldable ring. In some embodiments, the second gripping mechanism includes a second external gripping mechanism having a first distal barb configured to engage a third narrow portion of the distal foldable ring, a second distal barb configured to engage a fourth narrow portion of the distal foldable ring, a first proximal barb configured to engage a third narrow portion of the proximal foldable ring, and a second proximal barb configured to engage a fourth narrow portion of the proximal foldable ring. In some embodiments, the first gripping mechanism includes a first internal gripping mechanism configured to engage the first nesting rod and a second internal gripping mechanism configured to engage the second nesting rod. In some embodiments, the handle includes a slider mechanism operable to disengage the first proximal coupling mechanism from the first retracting rod and the second proximal coupling mechanism from the second retracting rod. In some embodiments, the distal foldable ring is engaged with the first retracting rod at a first engagement point, with the second retracting rod at a second engagement point, with the first nesting rod at a third engagement point, and with the second nesting rod at a fourth engagement point. In some embodiments, the first engagement point is disposed 180° opposite that of the second engagement point and the third engagement point is disposed 180° opposite that of the fourth engagement point. In some embodiments, the first retracting rod includes a first proximal prong, the second retracting rod includes a second proximal prong, the first nesting rod includes a third proximal prong, and the second nesting rod includes a fourth proximal prong. In some embodiments, the first and second proximal prongs are disposed proximal to the third and fourth proximal prongs when the flute is in the collapsed state. In some embodiments, the first retracting rod includes a first proximal prong, the second retracting rod includes a second proximal prong, the first nesting rod includes a third proximal prong, and the second nesting rod includes a fourth proximal prong. In some embodiments, the ring collar includes a first tab configured to engage a first slot of the first proximal prong, a second tab configured to engage a second slot of the second proximal prong, a third tab configured to engage a third slot of the third proximal prong, and a fourth tab configured to engage a fourth slot of the fourth proximal prong. In some embodiments, the ring collar includes a light source. In some embodiments, the flute includes at least one padding mechanism configured to engage an introitus of the patient.

In another aspect, embodiments of the present disclosure encompass systems and methods for dilating a vagina of a patient during a pelvic exam by a gynecologist. Exemplary methods may include engaging a handle with a flute when the flute is in an expanded state, where the flute includes a first retracting rod, a second retracting rod, a first nesting rod, a second nesting rod, a proximal foldable ring, and a distal foldable ring, and where the handle includes a first proximal coupling mechanism configured to releasably couple with the first retracting rod, a second proximal coupling mechanism configured to releasably couple with the first retracting rod, a first groove configured to at least partially receive the first nesting rod, a second groove configured to at least partially receive the second nesting rod, a first gripping mechanism and a second gripping mechanism operable to engage the flute when the proximal and distal foldable rings are in a folded orientation. Exemplary methods may also include transitioning the flute from the expanded state to the collapsed state, inserting the flute at least partially within the vagina of the patient while the flute is in the collapsed state, transitioning the flute from the collapsed state to the expanded state by disengaging the handle from the flute, and/or coupling a ring collar with the flute, where the ring collar operates to maintain the flute in the expanded orientation. In some cases, the flute is configured to transition between the expanded state where the proximal and distal foldable rings are in an unfolded orientation and the collapsed state where the proximal and distal foldable rings are in a folded orientation. In some cases, the handle is configured to maintain the flute in the collapsed state when the first proximal coupling mechanism is coupled with the first retracting rod, the second proximal coupling mechanism is coupled with the second retracting rod, and the first and second gripping mechanisms are engaged with the flute. In some cases, the ring collar is configured to engage the flute via the first and second retracting rods and the first and second nesting rods of the flute. According to some embodiments, the first proximal coupling mechanism includes a first proximal extrusion, the second proximal coupling mechanism includes a second proximal extrusion, the first retracting rod includes a first slot configured to engage the first proximal extrusion, and the second retracting rod includes a second slot configured to engage the second proximal extrusion. According to some embodiments, the first gripping mechanism includes a first external gripping mechanism having a first distal barb configured to engage a first narrow portion of the distal foldable ring, a second distal barb configured to engage a second narrow portion of the distal foldable ring, a first proximal barb configured to engage a first narrow portion of the proximal foldable ring, and a second proximal barb configured to engage a second narrow portion of the proximal foldable ring. According to some embodiments, the second gripping mechanism includes a second external gripping mechanism having a first distal barb configured to engage a third narrow portion of the distal foldable ring, a second distal barb configured to engage a fourth narrow portion of the distal foldable ring, a first proximal barb configured to engage a third narrow portion of the proximal foldable ring, and a second proximal barb configured to engage a fourth narrow portion of the proximal foldable ring. According to some embodiments, the first gripping mechanism includes a first internal gripping mechanism configured to engage the first nesting rod and a second internal gripping mechanism configured to engage the second nesting rod. According to some embodiments, the handle includes a slider mechanism operable to disengage the first proximal coupling mechanism from the first retracting rod and the second proximal coupling mechanism from the second retracting rod. According to some embodiments, the distal foldable ring is engaged with the first retracting rod at a first engagement point, with the second retracting rod at a second engagement point, with the first nesting rod at a third engagement point, and with the second nesting rod at a fourth engagement point. In some cases, the first engagement point is disposed 180° opposite that of the second engagement point and the third engagement point is disposed 180° opposite that of the fourth engagement point. According to some embodiments, the first retracting rod includes a first proximal prong, the second retracting rod includes a second proximal prong, the first nesting rod includes a third proximal prong, and the second nesting rod includes a fourth proximal prong. In some cases, the first and second proximal prongs are disposed proximal to the third and fourth proximal prongs when the flute is in the collapsed state. According to some embodiments, the first retracting rod includes a first proximal prong, the second retracting rod includes a second proximal prong, the first nesting rod includes a third proximal prong, and the second nesting rod includes a fourth proximal prong. In some cases, the ring collar includes a first tab configured to engage a first slot of the first proximal prong, a second tab configured to engage a second slot of the second proximal prong, a third tab configured to engage a third slot of the third proximal prong, and a fourth tab configured to engage a fourth slot of the fourth proximal prong. According to some embodiments, the ring collar includes a light source.

Other objectives of the disclosure will become apparent to those skilled in the art once the disclosure has been shown and described. These objectives are not to be construed as limitations of applicant's disclosure, but are merely aimed to suggest some of the many benefits that may be realized by the apparatus of the present application and with its many embodiments.

BRIEF DESCRIPTION OF THE DRAWINGS

Inventive features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 4 is a flow chart for a pelvic exam, according to embodiments of the present disclosure.

FIGS. 16A to 16C depict aspects of handles, according to embodiments of the present disclosure.

FIGS. 17A to 17C depict aspects of handles, according to embodiments of the present disclosure.

Figure 1:
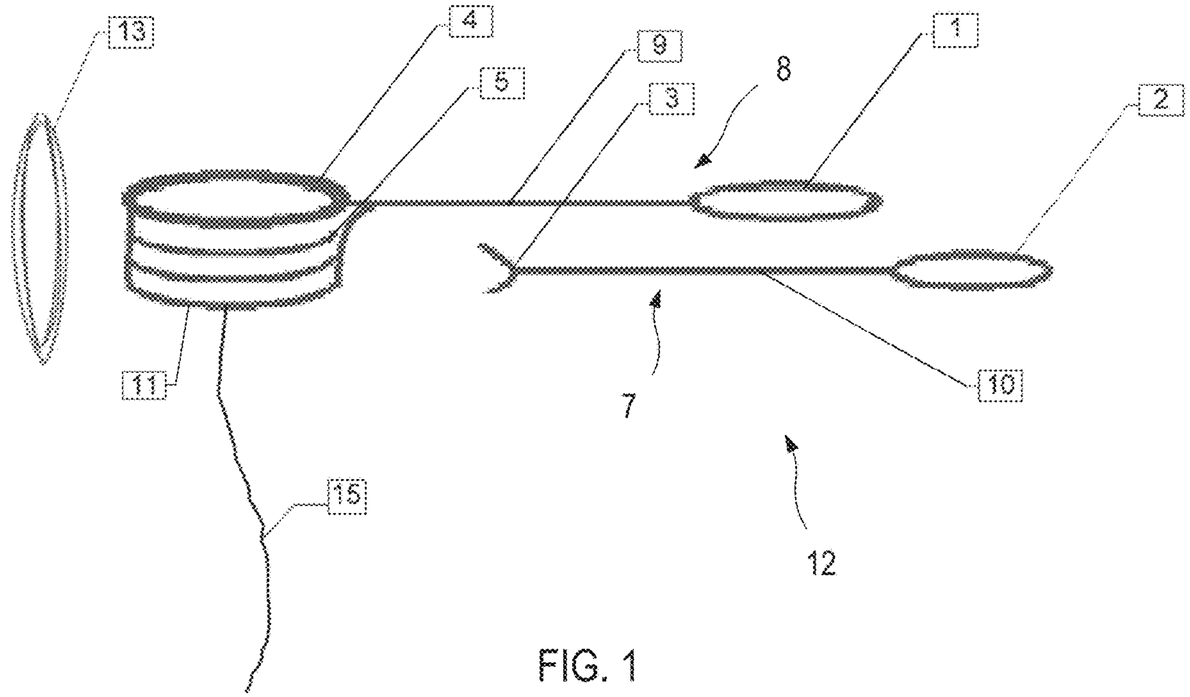
FIG. 1 provides an environmental view of an embodiment of a speculum in front of a vagina in a contracted position, according to embodiments of the present disclosure.

It is to be noted that the appended figures illustrate only exemplary embodiments of this disclosure and are therefore not to be considered limiting of its scope, for the disclosure may admit to other equally effective embodiments that will be appreciated by those reasonably skilled in the relevant arts. Also, figures are not necessarily made to scale but are representative.

DETAILED DESCRIPTION

Specific embodiments of the disclosed devices, systems and methods of use will now be described with reference to the drawings. Nothing in this detailed description is intended to imply that any particular component, feature, or step is essential to embodiments of the disclosure.

Disclosed are speculum embodiments and related methods to comfortably dilate a woman's vaginal canal during a pelvic exam. The details of exemplary embodiment are described with relevance to the figures.

Embodiments of the present disclosure encompass single-use vaginal speculum systems and methods that can be used for women's health exams. Exemplary devices can operate to create circumferential retraction of the vaginal tissue preventing or inhibiting vaginal prolapse. In some embodiments, exemplary devices can allow for enhances visualization of the vaginal canal, improving ease of use and exam efficiency. Additionally, exemplary devices can be used easily with one hand while allowing the other hand to perform with other necessary or desired procedural instruments.

In exemplary embodiments, a speculum can include a series of collapsible spiral rings that are fitted onto a tract of a slim elongated handle. The tract can be manipulated with a lever or other actuation mechanism to let the rings compress or decompress. In addition, a final ring collar can operate to enhance the speculum's stiffness to withstand tissue wall pressure. The ring collar can be provided with various options, including a single-use version with no LED lights and reusable version with LED lighting. The lighting can operate to improve visualization of the vaginal canal. The speculum can include two or more over molded rods to efficiently enable insertion and removal procedures.

In FIGS. 1 to 9 each component of a speculum embodiment or patient anatomy shown in the figures is labeled and indicated by the numeral as shown on this list: flute grip (1), expander grip (2), catch (3), lip (4), spine (5), sleeve (6), expander (7), flute (8), flute neck (9), expander neck (10), tunnel (11), speculum (12), vagina (13), cervix (14), thread (15), tilting hoop speculum (20), guide rod (21), LED flashlight or LED light guide (22), handle (23), drive mechanism or rotary dial (24), tilting hoop (25), driving piston (26), and hoop footer (27).

Figure 3:
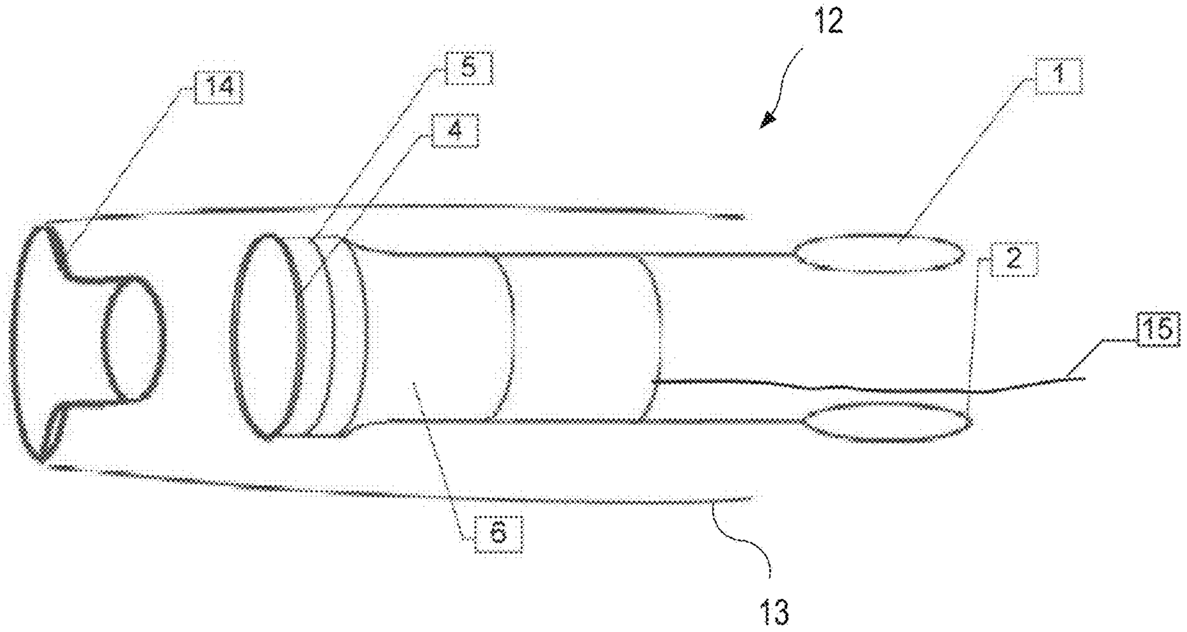
FIG. 3 is an environmental view of a speculum inside a vagina facing the cervix in an expanded position, according to embodiments of the present disclosure.

FIG. 1 is a perspective view of a preferred embodiment of a speculum 12. As shown, the speculum 12 is comprised of two parts, the flute 8 and the expander 7. The flute 8 may be comprised of a grip 1, a neck 9, and a tunnel 11. The grip 1 may be a single or double ellipsoid and configured to fit snugly in the palm of a hand. The neck 9 may be a thin rod which connects to the tunnel 11 on its proximal end and the grip 1 on its distal end. The tunnel 11 may be a hollow cylinder made of a clear or opaque film. The film, which may also be referred to as a sleeve 6 (e.g. as shown in FIG. 3), may take the shape of a cylinder because it is connected to circular supports called spines 5. The proximal spine 5 may be thicker than the other spines 5 and is referred to as a lip 4. A thread comprised of a piece of string is tied to a distal spine 5. The spines 5 are, in a preferred embodiment, circular and are often in a position correspondent to that of the lip 4. The entire tunnel 11 is manipulated by moving the lip 4.

The tunnel 11 and the spines 5 of which it is comprised, as shown in FIG. 1, are an important structure of the speculum 12 because it creates the structural support necessary to dilate the vagina 13. It also puts the necessary parts of the vagina 13 into view. The flute 8 and the expander 7 are accessory tools for the tunnel 11 used for the placement, and further structural support of the tunnel 11.

The expander 7 is a tool which may be used to place and move the tunnel 11. The expander 7 may be comprised of a catch 3, a neck 10, and a grip 2. Like the flute 8, the grip of the expander 2 is preferably an ellipsoid, and the neck of the expander 10 may be a thin rod. The catch 3 is on the proximal end of the expander. The catch 3 may be configured to hook the lip 4 of the flute 8 to manipulate the tunnel 11.

Other embodiments of the speculum 12 may be constructed from different materials or composites. However, a preferred embodiment of the speculum 12 can be constructed out of silicone. The speculum 12 may be made out of plastic or metal and lined with silicone.

Figure 2:
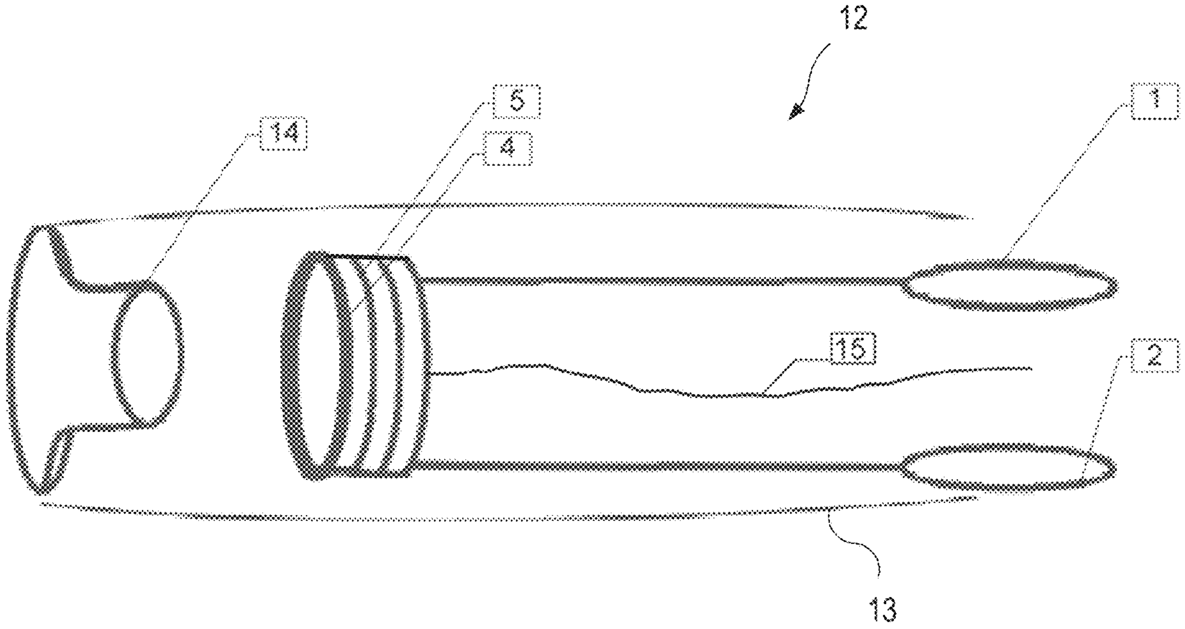
FIG. 2 is an environmental view of an embodiment of a speculum inside a vagina, in an intermediate position, according to embodiments of the present disclosure.

In one embodiment the tunnel has three positions, each having functional significance. These positions or states are "contracted" which is shown in FIG. 1, "intermediate" which is shown in FIG. 2, and "expanded" which shown in FIG. 3. When contracted, the lip 4 and axis of the tunnel 11 is facing upward and orthogonal to the cervix 14 and the tunnel 11 is compressed. The contracted position is the necessary position for placing the speculum 12 inside the vagina 13. The intermediate position is characterized by the lip 4 facing (coaxial) the cervix 14 and the tunnel 11 being compressed. The intermediate position is a position between the speculum 12 being placed and being used. The expanded position is characterized by the lip 4 facing (coaxial) the cervix 14 and the tunnel 11 being expanded. In the expanded position the speculum 12 is functional, dilating the vagina 13 and putting the cervix 14 and vagina 13 in view.

FIG. 1 shows the speculum 12 in its contracted state. The tunnel 11 is compressed, and all the spines 5 are stacked together. The lip 4 is orthogonal to the neck of the flute 8. This is the state the speculum 12 is in before the flute 8 is inserted into a vagina 13. The expander 7 is also separate from the flute 8 at this point.

FIG. 2 is a perspective view of the speculum 12 inside a representation of a vagina 13. The grips 1 & 2 are used to place the tunnel 11 inside the vagina 13. The expander 7 is kept outside the vagina while still connected to the constricted tunnel 11 during insertion. The necks of the expander 7 and flute 8 are the length of a vagina 13 or longer. The speculum 12 is customizable. One size fits many, independent of vaginal depth. If a vagina 13 has a smaller diameter, then a tunnel 11 with a smaller diameter may be used. A smaller tunnel 11 may be used with the same flute 8 and expander 7. This figure also shows the lip 4 as parallel to the neck 9 of the flute 8, and facing the cervix 14. The spines 5 may be thicker or stronger in various degrees for patients who are obese or experience pelvic prolapse.

FIG. 3 is an environmental view of the speculum 12 inside the vagina 13 in an expanded state. Both the flute 8 and the expander 7 are inside the vagina 13 to the depth of the grips. The thread 15 has been engaged to pull the sleeve 6 down the length of the necks of both the flute 8 and the expander 7. The necks support the spines 5 of the tunnel 11. These structures are suitably designed to counteract the compressive forces of the vaginal walls. The lip 4 is facing (coaxial) the cervix 14 and the cervix 14 is in view through the tunnel 11. The sleeve 6 may preferably be made out of a clear material so that the vaginal walls are also in view.

FIG. 4 shows a flow chart of a pelvic exam which follows the same steps as the exam described below. The speculum 12 is to be used during a pelvic exam to allow a medical provider or gynecologist the ability to view the vaginal walls and cervix 14. Referring to Step A of FIG. 4, the exam begins by first having a patient disrobe. If the gynecologist is a male, a chaperone should be present. The patient is disrobed from the waist down and wrapped in a gown. Next, referring to Step B, the patient will lie on their back on an exam table with their feet placed in stirrups. The patient slides to the end of the table and lets their knees open. Consent is obtained and the medical provider outlines each step of the process before the examination beings. During Step C as per FIG. 4, the gynecologist may begin the external visual exam looking at the vulva for irritation, redness, or other abnormalities. Next, the gynecologist will use the speculum 12 of the specification to dilate the vaginal walls.

In Step E outlined by the flow chart in FIG. 4, the speculum 12 is inundated in a lubricant and warmed. At this point, the flute 8 and the expander 7 are held by the grips in front of the vagina 13 by the hands of the gynecologist, with the flute 8 in one hand and the expander 7 in another. The tunnel 11 is in a contracted position. The lip 4 of the tunnel and the plurality of spines 5 are facing upward. The spines 5 are stacked on top of one another. The sleeve 6 is compressed together and not taught.

Still referring to FIG. 4, the gynecologist will then instruct the patient to relax their muscles. Then the gynecologist places the tunnel 11 into the vagina 13 via the flute 8 to a necessary depth. The expander 7 is then placed into the vagina 13. The catch 3 of the expander hooks the lip 4 of the tunnel 11 and pulls the lip 4 down. This pulling causes the lip 4 to rotate. The lip 4 is rotated until it faces the cervix. The expander 7 is still latched to the lip via the catch 3. Now, the thread 15 is pulled out of the vagina 13. The sleeve 6 is unfurled and the material which comprises it is taught. The spines 5 are pulled apart. The tunnel 11 is now fully expanded. The tunnel 11 in its now expanded state provides structural support against the vaginal canal keeping the vagina 13 dilated.

The gynecologist is now able to observe the cervix 14 and the vaginal walls. Referring to FIG. 4, Step J, if a pap test is deemed necessary the gynecologist will take a sample of cervical cells. Lastly, the gynecologist will palpate the vaginal canal in an attempt to feel for similar abnormalities. During palpation the doctor will also feel the abdomen and pelvis since some organs like the uterus and ovaries cannot be seen. Then the speculum 12 is ready to be contracted. First the gynecologist uses the catch 3 of the expander 7 to hook the lip 4 of the tunnel. The gynecologist then uses the catch 3 of the expander 7 to compress the sleeve 6 and consequently, the tunnel 11. The sleeve 6 is furled and the spines 5 sit next to each other. Then the doctor uses the expander 7 to rotate the lip 4 so that the lip 4 is now orthogonal to the cervix 14. The expander 7 is then pulled out of the vagina 13 via the grip. Shortly after, the flute 8 is removed from the vagina 13 via the grip. The examination is over. Lastly, the patient may sit up, get off the exam table, and clothe themselves.

Figure 5:
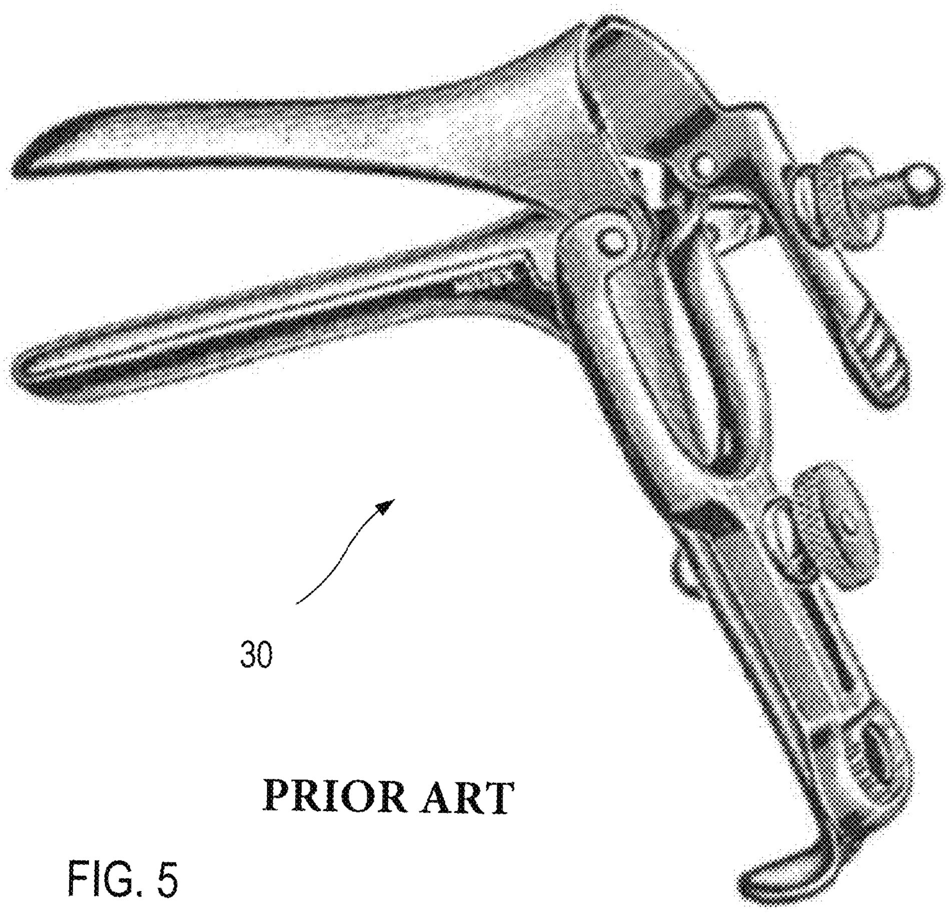
PRIOR ART FIG. 5
FIG. 5 is a conventional speculum.

FIG. 5 depicts a conventional speculum 30. Such vaginal speculums have a duck bill shape that is placed in the vagina to examine, diagnose, and treat various conditions. These traditional speculum designs date back to 1845, and typically include two sides to retract the vaginal walls, while failing to retract the vaginal side walls. Hence, the side walls often protrude into the viewing area of the device, obstructing the visualization of the distal vagina, fornix and cervix. For obese women, the handle of the conventional speculum tends to prevent the advancement of the device into the vagina as it is obstructed by the patient's bottom. These situations cause the providers to open the speculum wider or use a different wider billed speculum which can create pain, discomfort and potential tearing of the vaginal tissue. Conventional speculums are typically manufactured out of metal or plastic. The metal speculums tend to be cold, require repeat sterilization, and create metal clicking sounds. The plastic speculums tend to have smaller visualization windows, clicking sounds and create a larger environmental landfill risk. Conventional speculums often contain an obtrusive handle, pose discomfort and pain to patients, and include hinged openings and wide openings allowing for prolapse.

Figure 6:
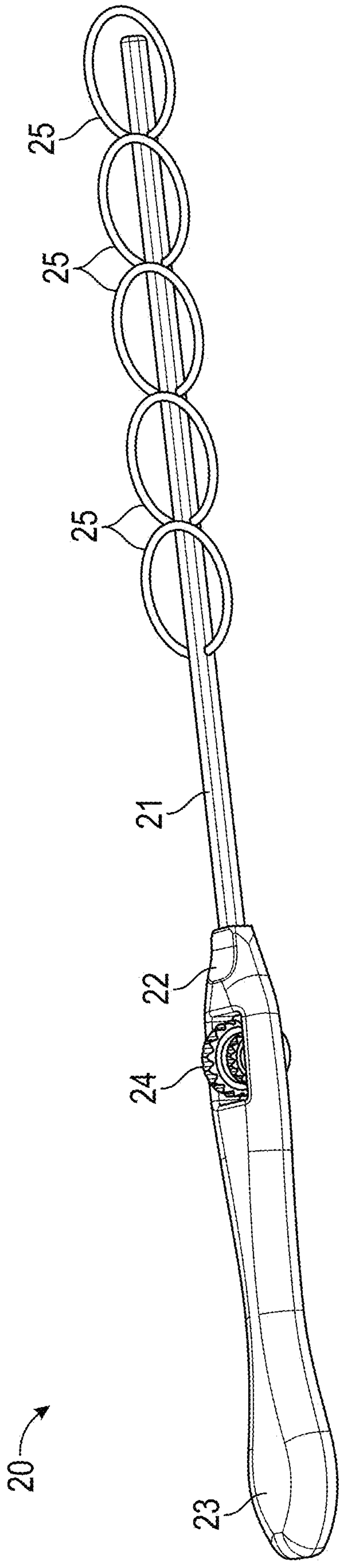
FIG. 6 is a tilting hoop speculum in a retracted state, according to embodiments of the present disclosure.

FIG. 6 is a perspective view of the preferred embodiment of a tilted hoop speculum 20. As shown, the speculum 20 can include a guide rod 21. The tilting hoop speculum 20 is depicted here in its retracted state. The tunnel defined by a plurality of tiltable hoops 25 is compressed, and all the hoops 25 are tilted against the guide rod 21. The hoops 25 are parallel to the neck of the handle 23. This is the state the speculum 20 is in before the handle 23 is used to move the guide rod 21 into a vagina. The rotary dial 24 is in the handle is in a first position at this point. The tilting hoop speculum 20 can include an LED flashlight or LED light-guide 22.

Figure 7:
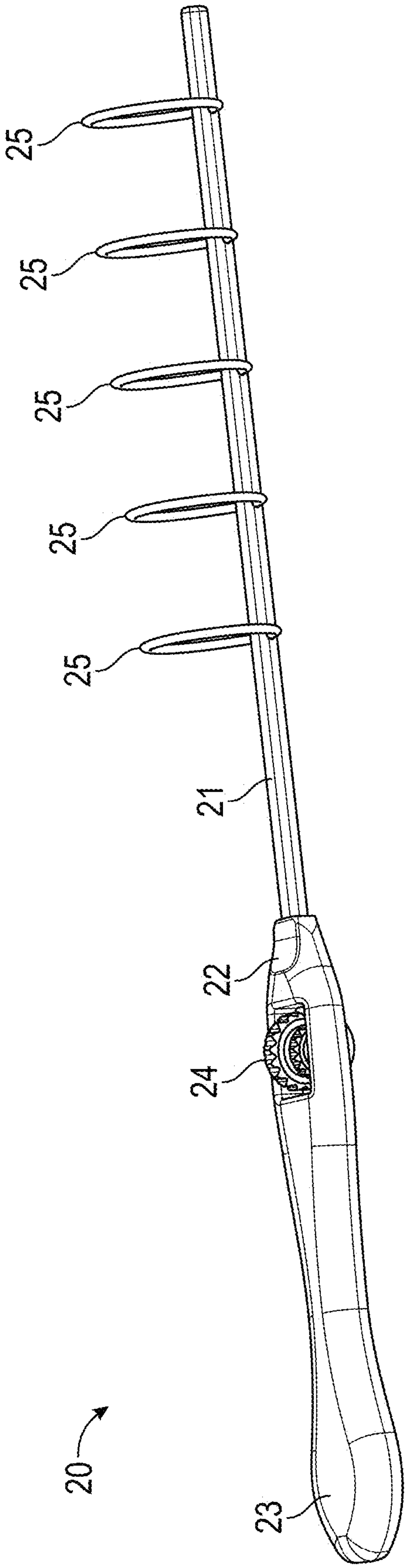
FIG. 7 is a tilting hoop speculum in a deployed state, according to embodiments of the present disclosure.
Figure 8:
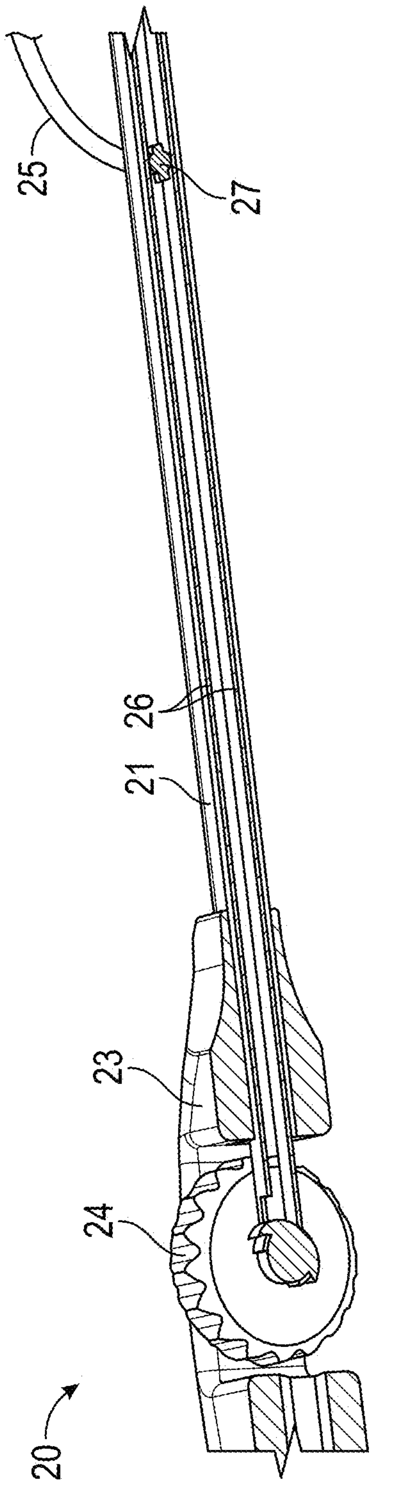
FIG. 8 is a view of a drive mechanism of the tilting hoop speculum in a retracted state, according to embodiments of the present disclosure.

FIG. 7 is a perspective view of the speculum 20. The handle 23 is used to place the guide rod 21 and hoops inside a vagina (not shown). in some embodiments there is an LED or flashlight 22 at the end of the handle 23 to act as a guide light for insertion of the guide rod 21 into a vagina (not shown). The rotary dial 24 is kept outside the vagina (not shown) but still connected to the constricted tunnel (plurality of hoops 25) during insertion via pistons 26 (e.g. as shown in FIG. 8). The guide rod 21 and handle 23 are the length of a vagina (not shown) or longer. The speculum 20 is customizable. One size fits many, independent of vaginal depth. If a vagina (not shown) has a smaller diameter then a hoop 25 with a smaller diameter may be used. A smaller hoop 25 may be used with the same handle 23 and an expander 7. FIG. 7 also shows the hoops 25 as orthogonal to the guide rod 21 in a deployed position so that the hoops may be interfacing the cervix (not shown) when inserted into a vagina (not shown). The hoops 25 may be thicker or stronger in various degrees for patients who are obese or experience pelvic prolapse.

FIG. 7 may be considered an environmental view of the speculum 20 inside the vagina (not shown) in a deployed state. The guide rod 21 and hoops 25 have been inside the vagina (not shown) to the depth of the handle 23. The rotary dial 24 has been moved to a second position to tilt the hoops up over the length of the guide rod 21. The guide rod 21 support the hoops 25 of the tunnel. These hoop structures are suitably designed to counteract the compressive forces of the vaginal walls. The first hoop is facing (coaxial) the cervix (not shown) and the cervix (not shown) is in view through the tunnel defined by the hoops 25. A sleeve (not shown) may cover the hoops 25 to form a tunnel and preferably be made out of a clear material so that the vaginal walls are also in view.

Figure 9:
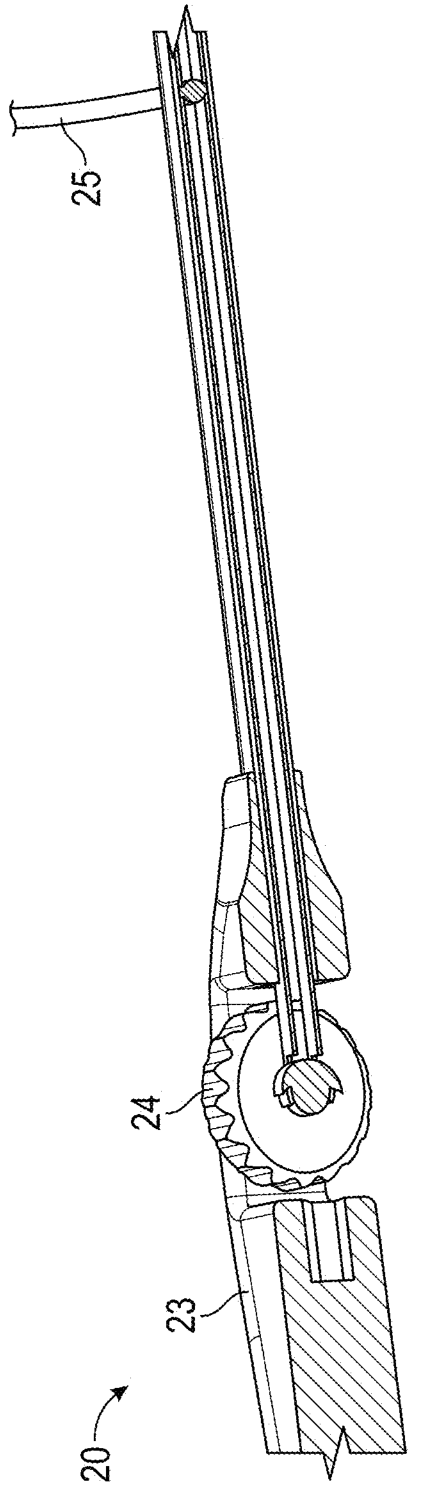
FIG. 9 is a view of a drive mechanism of the tilting hoop speculum in a deployed state, according to embodiments of the present disclosure.

FIGS. 8 and 9 shows a cross section of the speculum 20. As shown, the rotary dial 24 is connected at a centerpiece to two piston rods 26 that are further connected to a foot 27 of the hoops 25. When the rotary dial 24 is rotated, the pistons 26 move to-and-fro to tilt the hoops 25 between the retracted position (FIGS. 6 and 8) on one hand and the deployed position (FIGS. 7 and 9) on the other hand.

A flow of a pelvic exam follows the same steps as the exam described below. The speculum 20 is to be used during a pelvic exam to allow a medical provider or gynecologist the ability to view the vaginal walls and cervix. The exam begins by first having a patient disrobe. If the gynecologist is a male, a chaperone should be present. The patient is disrobed from the waist down and wrapped in a gown. Next, the patient will lie on their back on an exam table with their feet placed in stirrups. The patient slides to the end of the table and lets their knees open. Consent is obtained and the medical provider outlines each step of the process before the examination beings. At this point, the gynecologist may begin the external visual exam looking at the vulva for irritation, redness, or other abnormalities. Next, the gynecologist will use the speculum 20 of the specification to dilate the vaginal walls.

More specifically, the speculum 20 is inundated in a lubricant and warmed. At this point, the handle 23 is held in front of the vagina (not shown) by the hands of the gynecologist, with the handle 23 in one hand. The tunnel is in a retracted position. The hoop of the tunnel and the plurality of hoops 25 are facing upward. The hoops are stacked on top of guide rod 21.

The gynecologist will then instruct the patient to relax their muscles. Then the gynecologist places the guide rod 21 into the vagina (not shown) via the handle 23 to a necessary depth. The dial 24 is then rotated so that the hoops 25 rotate. The hopes 25 are rotated until they faces the cervix. The dial may suitably feature detents to lock the speculum in a deployed state. The tunnel of hoops 25 is now fully expanded. The tunnel of hoops 25 in its now expanded state provides structural support against the vaginal canal keeping the vagina (not shown) dilated.

The gynecologist is now able to observe the cervix and the vaginal walls. If a pap test is deemed necessary the gynecologist will take a sample of cervical cells. Lastly, the gynecologist will palpate the vaginal canal in an attempt to feel for similar abnormalities. During palpation the doctor will also feel the abdomen and pelvis since some organs like the uterus and ovaries cannot be seen. Then the speculum 20 is ready to be contracted. First the gynecologist uses the rotary dial to rotate the hoops of the tunnel to a retracted position. The sleeve 6 is retracted and the hoops 25 sit next to flat along the guide rod 21. The guide rod 21 is then pulled out of the vagina (not shown) via the handle 23. The examination is over. Lastly, the patient may sit up, get off the exam table, and clothe themselves.

Figure 10A:
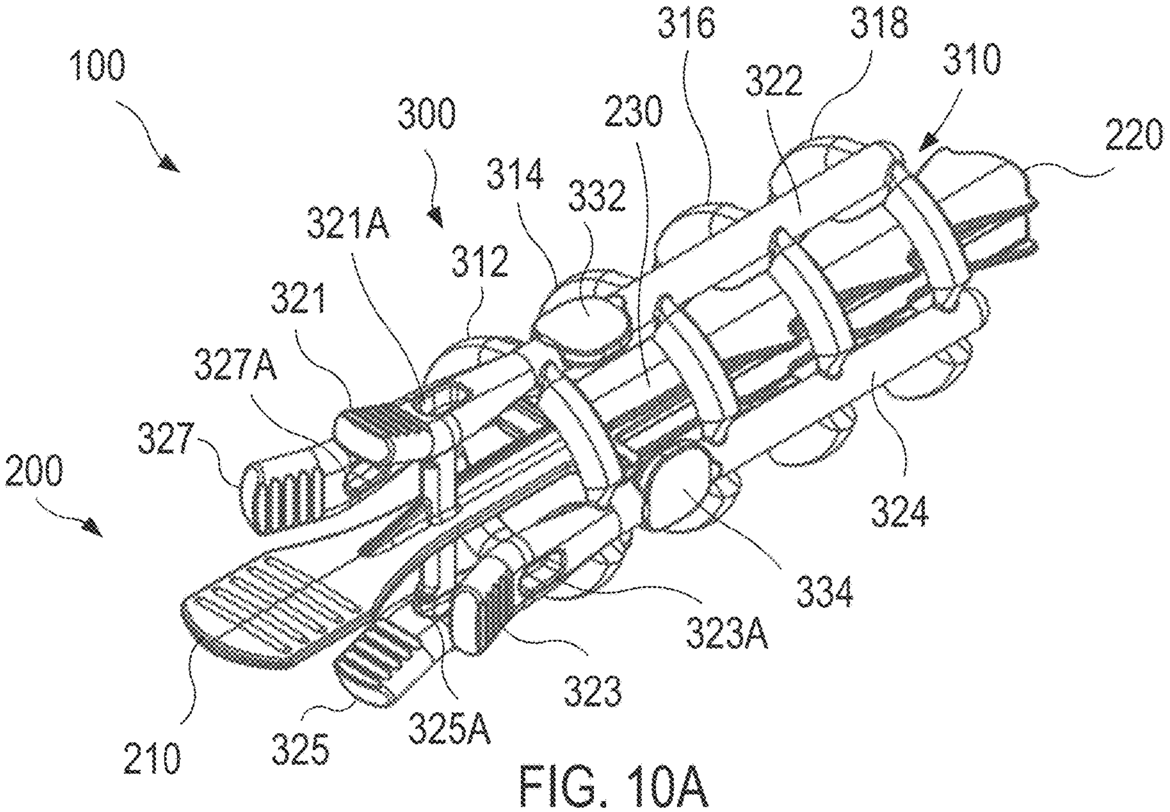
FIGS. 10A to 10C depict aspects of speculum systems, according to embodiments of the present disclosure.
Figure 10B:
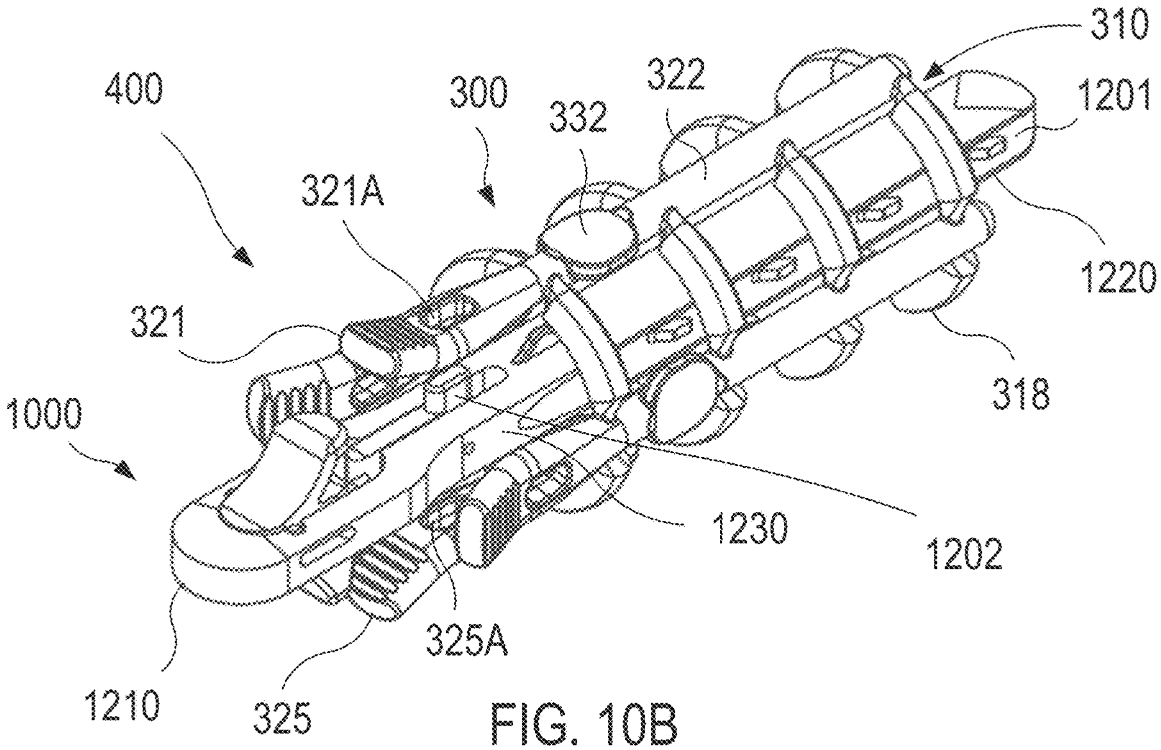
Figure 11A:
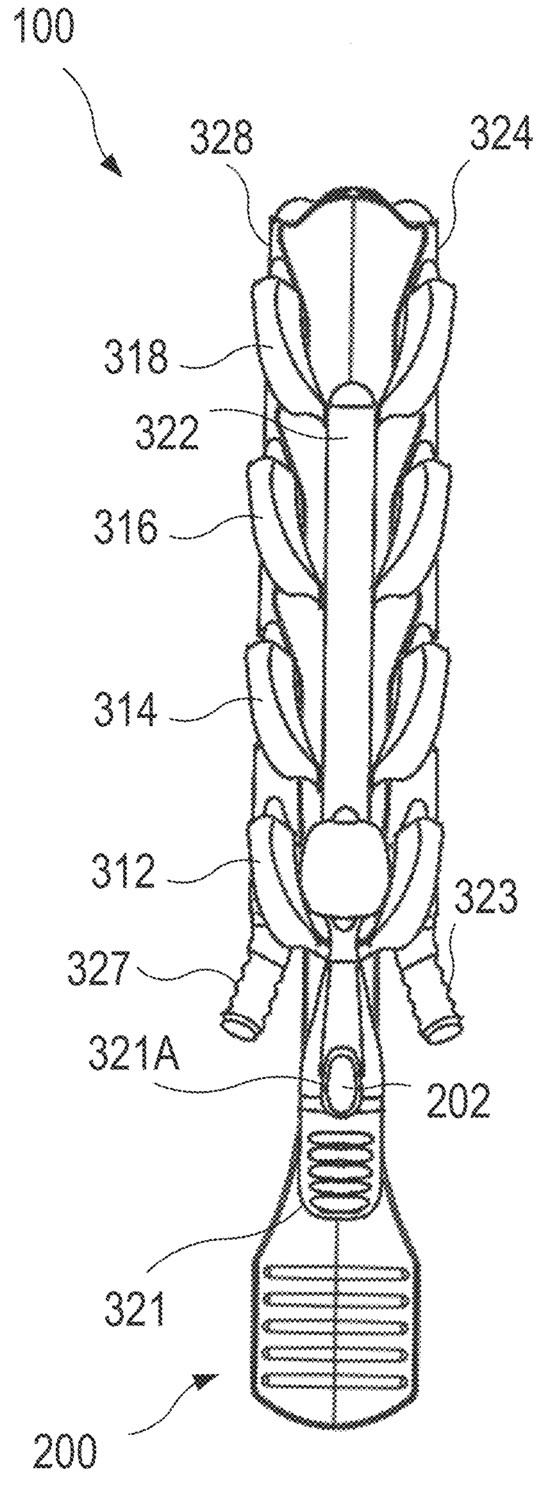
FIGS. 11A to 11D depict aspects of speculum systems, according to embodiments of the present disclosure.
Figure 11B:
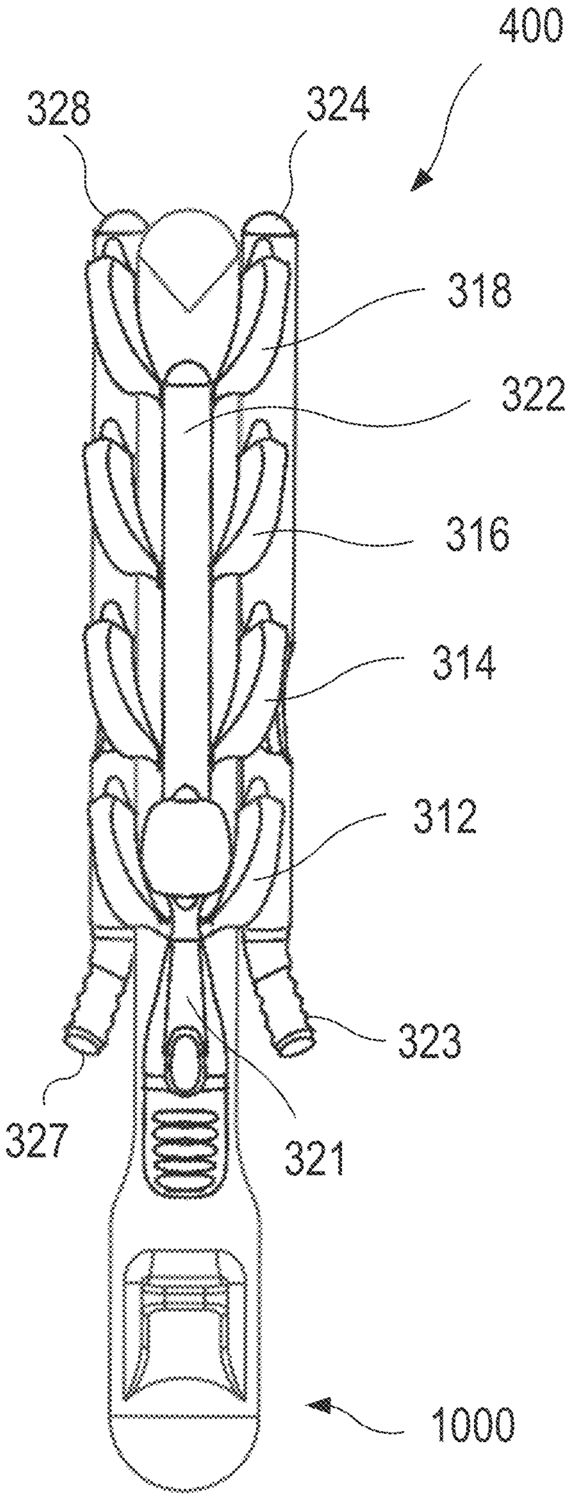

FIGS. 10A and 10B respectively depict comparative aspects of a speculum or speculum system 100 and a speculum or speculum system 400, according to embodiments of the present disclosure. In some cases, speculum 100 is a single use speculum. In some cases, speculum 400 is a single use speculum. In the embodiments shown here, the flute 300 or the tunnel 310 of the flute 300 is in an open or expanded configuration. FIGS. 11A and 11B depict embodiments where the speculums 100, 400 are in a compressed configuration. The handles 200, 1000 can be referred to as insertion handles.

Speculum embodiments disclosed herein can be provided as a collapsible device configured with rings connected with multiple (e.g. four) rods. In some cases, of the four rods, two can be over molded with plastic to enhance insertion and removal procedures. In some cases, one or more rods can have slots or engagement mechanisms to connect with the slim elongated handle and the ring collar. In some cases, the slim elongated handle allows for the collapsed speculum to be inserted into the vaginal canal and the ring collar can keep the speculum in its expanded position. Aspects of a speculum can be configured to vary in length, cross-sectional area, and diameter. In some cases, speculums may vary in the number and size of rings and/or rods they include. In some cases, a speculum or component thereof may include a light feature to enhance visualization. In some cases, a speculum or component thereof may feature different or desired geometries to enhance light distribution. In some cases, one or more components of a speculum can be made or include biocompatible rigid polymers and/or rubbers. In exemplary embodiments, speculums disclosed herein have no handle feature that would interfere with a patient's bottom. In some cases, exemplary speculum configurations can provide a 360-degree opening view. In some cases, exemplary speculum configurations can be used in any direction circumferentially. In some cases, exemplary speculum configurations are malleable to adjust naturally with vaginal wall pressure. In some cases, exemplary speculum configurations can be used with one hand. Embodiments of the present disclosure encompass speculum configurations that enable the end user to insert the device in a linear motion into the vaginal canal without any interference with residing anatomy. Exemplary devices can operate to expand to contour around the vaginal canal pressure, allowing for natural adjustability. In exemplary embodiments, one or more components of a speculum device can be made of or include rubber to improve comfort. A ring core or collar can be added to the end to keep the device expanded enough to allow for view of the cervix. In some cases, a ring core or collar can include one or more LED lights to allow for enhanced visualization. Exemplary ring collars can operate to allow for the device to remain in the vaginal canal so the user's hands are free to use for other instruments and procedures. The ring collar can then be removed so the speculum can be compressed for removal. In exemplary embodiments, a speculum can be provided as a multi-material, single-use vaginal speculum that contains geometry that allows for radial expansion of the vaginal canal to enhance viewing and ease of vaginal exams. Speculum configurations or components thereof can be provided in any of a variety of sizes, materials, and/or colors. Insertion handle geometries can be provided in a wide variety of configurations. Flute embodiments can include any desired number of rods and/or rings.

With returning reference to FIG. 10A, speculum 100 includes a handle 200 and a flute 300 that can be loaded onto the handle 200. Additional aspects of the handle 200 can be further understood with reference to FIGS. 16A to 16C. As shown in FIG. 10A, handle 200 can include a proximal section 210, a distal section 220, and a medial section 230 disposed between the proximal section 210 and the distal section 220. The flute 300 can include one or more rings (e.g. rings 312, 314, 316, and 316) which so as to define or provide a tunnel 310 into which at least a portion of the handle 200 may be placed. The rings of the flute 300 can be supported by one or more rods, and each rod can include a proximal prong. For example, rod 322 includes proximal prong 321 and rod 324 includes proximal prong 323. This embodiment includes two additional rods having proximal prong 325 and proximal prong 327 respectively. In some cases, a flute can include one or more padding mechanisms or introitus pads. For example, as shown here, flute 300 includes padding mechanisms or introitus pads (e.g. 332, 334). Such a padding mechanism can be coupled with or disposed on a flute. In exemplary embodiments, a padding mechanism includes or is made of a compressible material. A padding mechanism can operate to support and/or engage the vaginal introitus of a patient. In some cases, a physician or other health provider can use one or more of the padding mechanisms as a depth indicator or depth control mechanism, whereby the action of lining up the padding mechanisms with the introitus of the patient can ensure that the flute is inserted into the vagina at the desired or appropriate depth. In some cases, a padding mechanism can be coupled with a rod of the flute. In some cases, each individual rod of a flute includes or is coupled with a corresponding individual introitus pad. In some cases, a flute or at least one rod includes a circumferential protrusion or padding mechanism configured to support and/or engage the introitus.

Figure 10C:
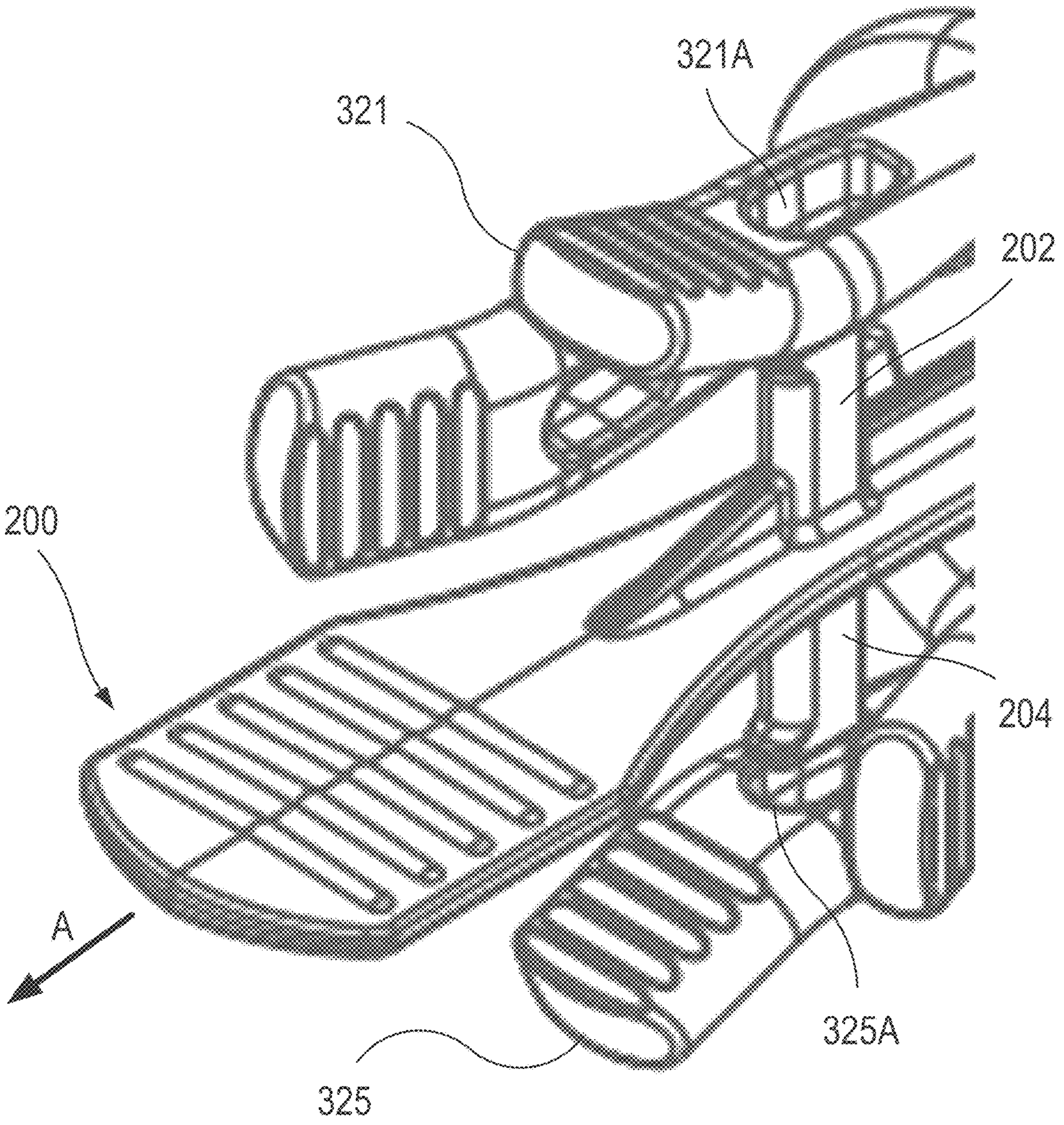

The handle 200 can include one or more extrusions or other connection mechanisms by which one or more rods of the flute 300 can be mechanically coupled with the handle 200. For example, handle 200 can include one or more proximal extrusions 202, 204 as depicted in FIGS. 16A to 16C which can engage or be mechanically coupled with one or more prong slots, respectively. With reference to FIG. 10C, it can be seen, for example, that slot 321A of prong 321 can be placed to engage extrusion 202 of handle 200. Likewise, slot 325A of prong 325 can be placed to engage extrusion 204 of handle 200.

With the prong slots 321A, 325A and corresponding handle proximal extrusions 202, 204 engaged with one another, the handle 200 can be retracted proximally relative to the flute 300 as indicated by arrow A, thereby drawing prongs 321 and 325 of the flute in a relatively proximal direction as well. As a result, the rings 312, 314, 316, 318 of the flute become folded, as rod 322 and the rod laterally opposed from rod 322 (hidden from view, rod 326) are pulled proximally relative to rods 324 and 328, as shown in FIG. 11A. As discussed elsewhere herein, in some cases rods 324 and 328 can be referred to as nesting rods, as they can be positioned to nest at least partially within respective grooves of the handle. With reference to FIGS. 10A, 10C, 11A, 11C, and 16B in combination, it can be seen that when retracting rods 322, 326 are drawn proximally, nesting rods 324, 328 can be at least partially positioned within grooves 201, 203 respectively, slot 323A of prong 323 can be placed to engage medial extrusion 217 of handle 200, and slot 327A of prong 327 can be placed to engage medial extrusion 219 of handle 200.

Figure 11C:
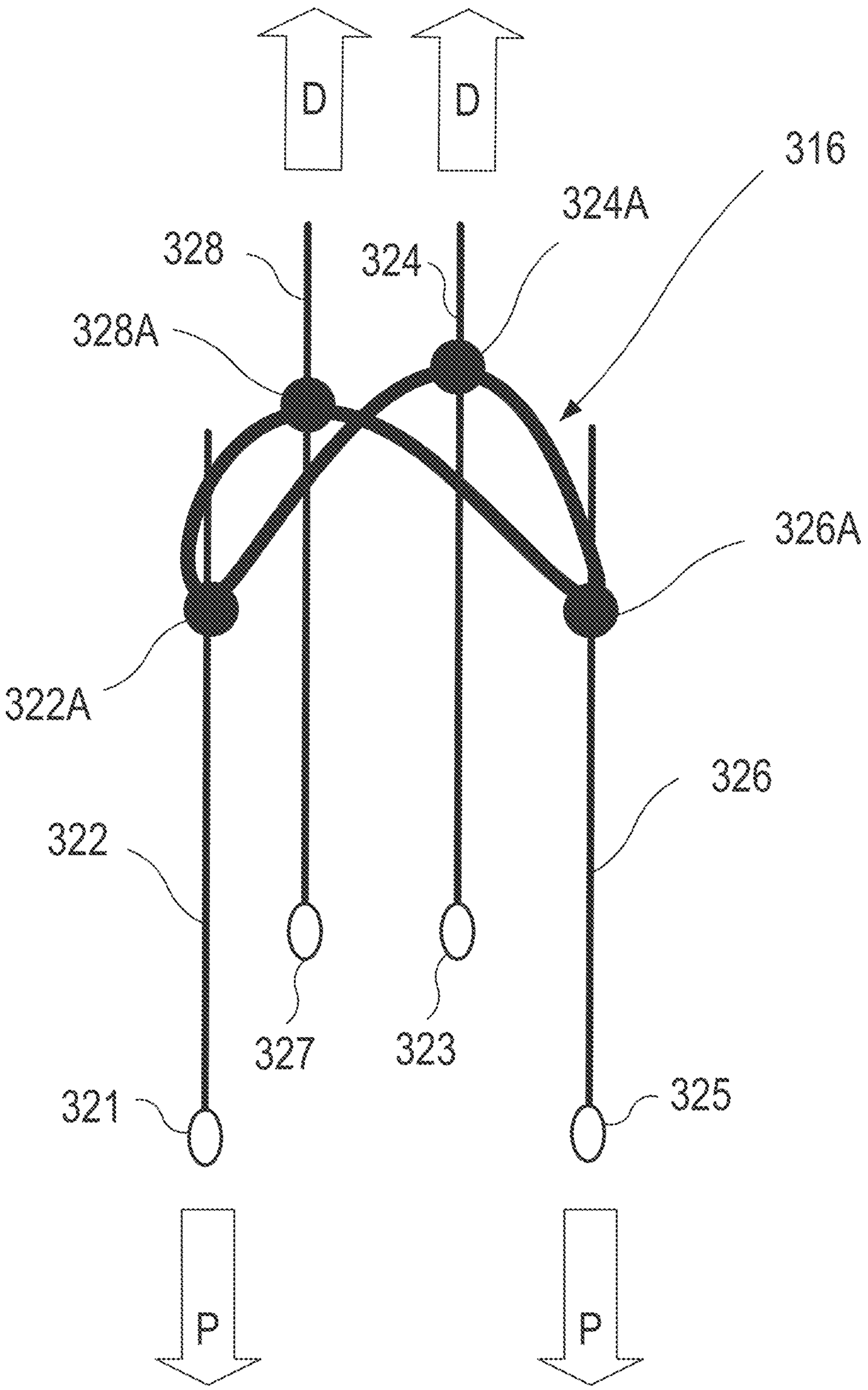

FIG. 11C depicts additional aspects of the ring folding process, according to embodiments of the present disclosure. As shown in this schematic representation, a ring (e.g. 316) can be attached or engaged with rods 322, 324, 326, and 328 at engagement points 322A, 324A, 326A, and 328A respectively. When the handle (not shown) is drawn in a proximal direction, the prongs 321, 325 are also consequently drawn in the proximal direction as indicated by arrows P. Alternatively, rods 324, 328 can be advanced distally as indicated by arrows D. In some cases, folding of the rings can be achieved by combined movement of the rods, for example moving rods 322 and 326 proximally and also moving rods 324 and 328 distally. As shown here, when rods are moved, the ring 318 can assume a configuration which can be referred to as a folded ring or a wave ring. The configuration can be considered to have two peaks (e.g. at points 324A and 328A) and two valleys (e.g. at points 322A and 326A). This folding action can reduce the profile of the ring. To hold the rings in a folded configuration, external gripping features of the handle can be engaged with the rings. As shown in FIG. 16B, handle 200 includes a plurality of external gripping mechanisms 251, 252, 253, 254, 255, and 256. In some cases, an external gripping mechanism can be provided as a barb, a shark fin, a hook, or the like.

Figure 11D:
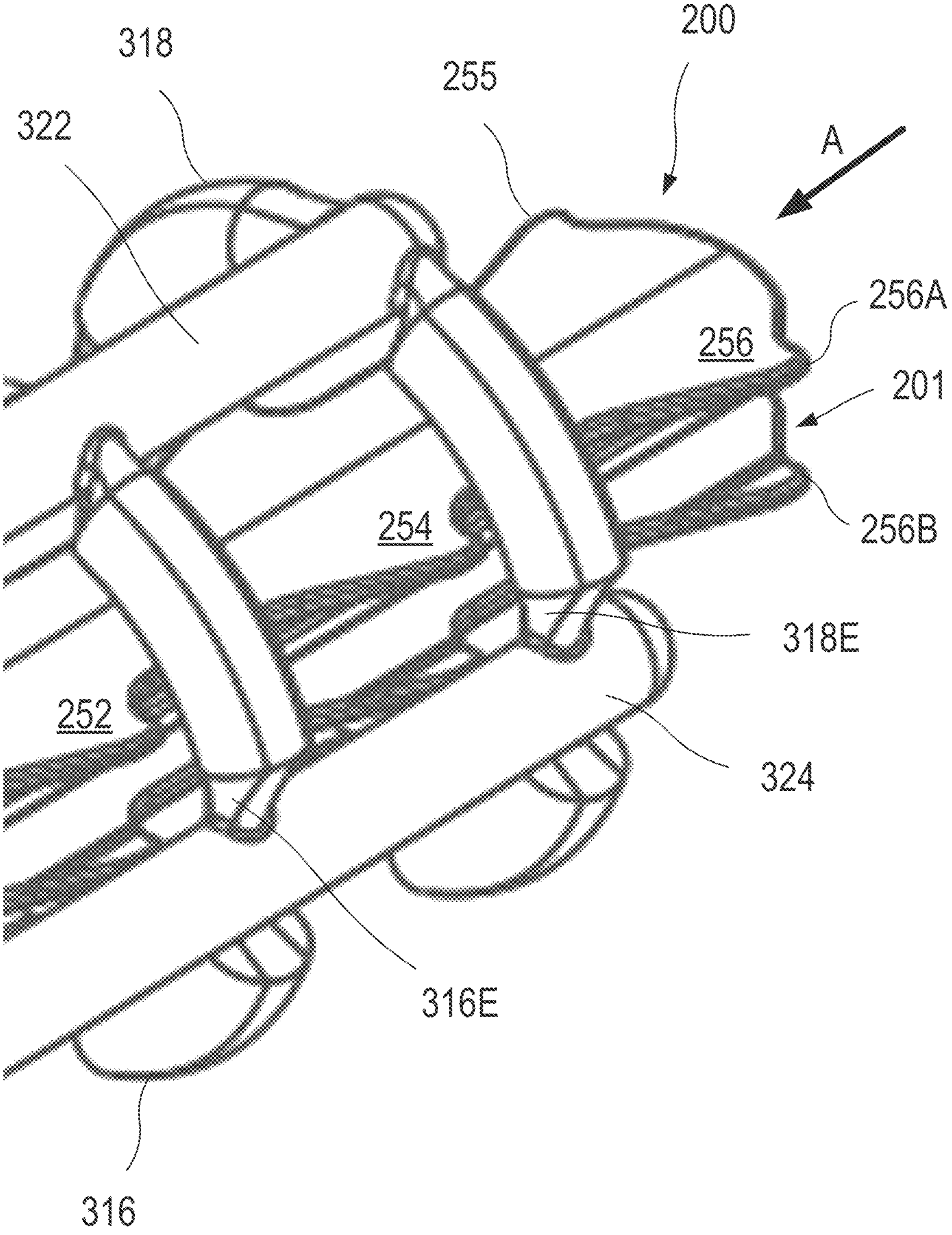

With reference to FIG. 11D, it can be seen that after handle 200 is moved in a proximal direction relative to the flute as indicated by arrow A (which also moves rod 322 in the proximal direction), external gripping mechanism 256 can be engaged with an engagement portion 318E of ring 318. Likewise, external gripping mechanism 255 can be engaged with another engagement portion on the opposing side of the ring. In some cases, as shown here, an engagement portion of the ring can be a narrowed or smaller diameter portion of the ring. Multiple external gripping mechanisms can be engaged with multiple rings, respectively. For example, as shown here, external gripping mechanism 254 can be engaged with an engagement portion 316E of ring 316. In some cases, external gripping mechanisms can be provided in pairs or other multiples. For example, external gripping mechanism 256 can be provided as a first external gripping mechanism 256A and a second external gripping mechanism 256B. In such cases, a first external gripping mechanism 256A could engage a first engagement portion of the ring and the second external gripping mechanism 256B could engage a second engagement portion of the ring. As illustrated in FIG. 11D, the handle 200 can include grooves or recesses that are configured to accept rods when the rings are folded. For example, as rings 316, 318 are folded when handle 200 is drawn proximally, nesting rod 324 can be positioned at least partially within groove 201.

Figure 12:
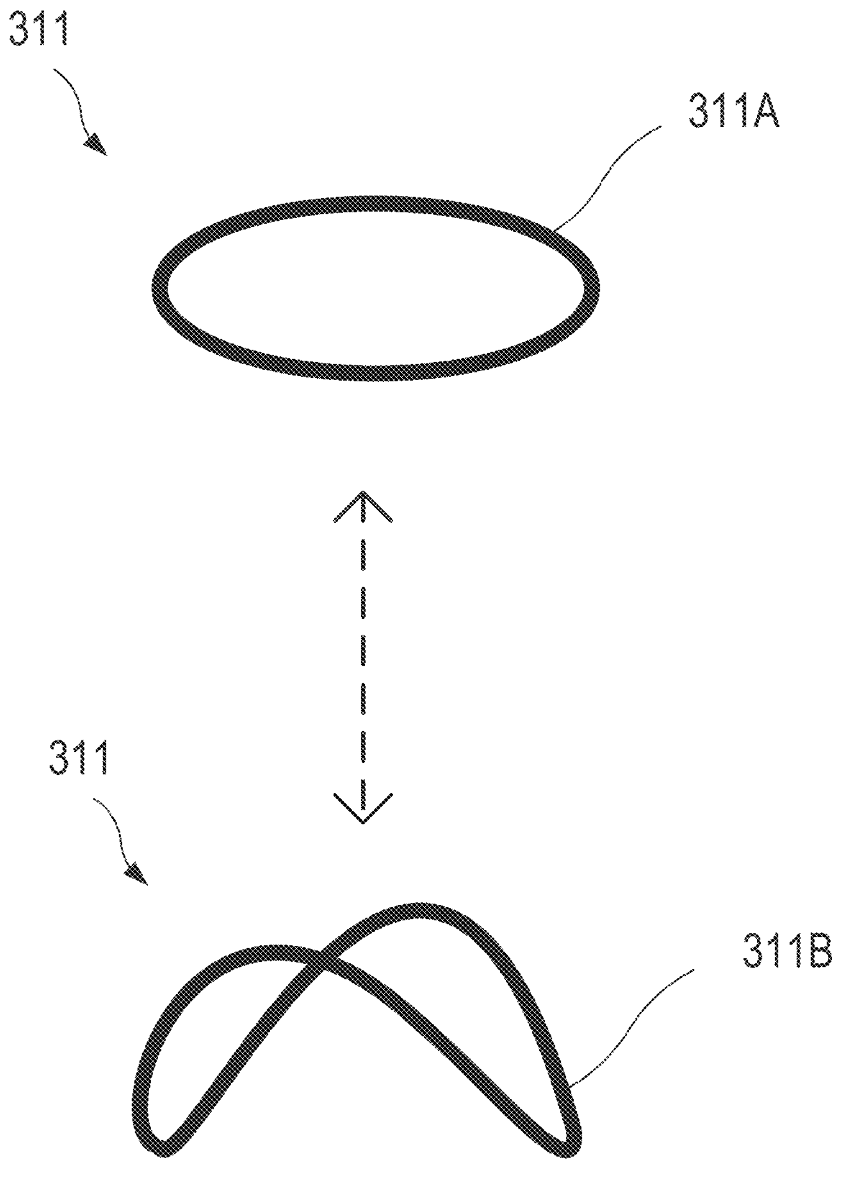
FIG. 12 depicts aspects of a flute ring, according to embodiments of the present disclosure.

Once the external gripping mechanisms have been engaged with the rings, the handle effectively operates to hold the rings in the folded orientation, and thus the flute is maintained in a low profile, contracted, or constrained configuration (e.g. as shown in FIG. 11A). While in this low profile or constrained configuration, the flute can be inserted into the patient. Once positioned as desired within the patient, the handle can be disengaged from the flute, for example with reference to FIG. 10C by removing prongs 321 and 325 from extrusions 202 and 204 respectively. According to some embodiments, the rings can be manufactured or provided so that they are biased toward an unfolded configuration, such that when the folding forces which were previously applied to the rings are subsequently removed, the rings return to their unfolded orientation, thus allowing the flute to return to an expanded or unconstrained configuration (e.g. as shown in FIG. 10A). As shown in FIG. 12, a ring 311 can transition back and forth between an unfolded or decompressed configuration 311A (where no folding force is applied to the ring) and a folded or compressed configuration 311B (where a folding force is applied to the ring).

Figure 13:
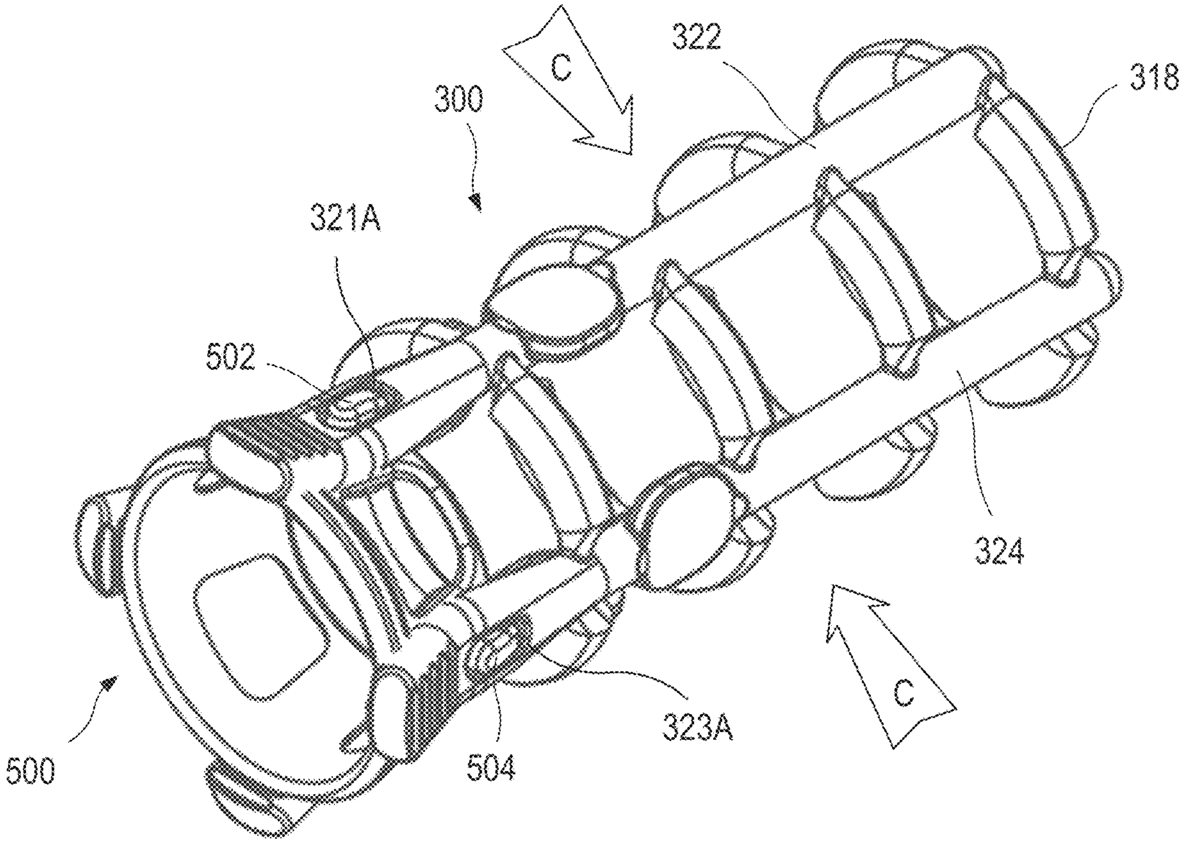
FIG. 13 depicts aspects of a flute and ring collar, according to embodiments of the present disclosure.

As shown in FIG. 13, when the flute 300 is in the expanded configuration, a ring collar 500 can be engaged or attached with the flute. In some cases, the ring collar 500 can include one or more tabs (e.g. 502, 504) configured to engage respective prong slots (e.g. 321A, 323A) of the flute. When the ring collar 500 is engaged with the flute 300, it operates to hold the flute in the expanded configuration and the rings in the unfolded orientation, even when compressive forces are applied against the flute as indicated by arrows C.

Figures 14A, 14B:
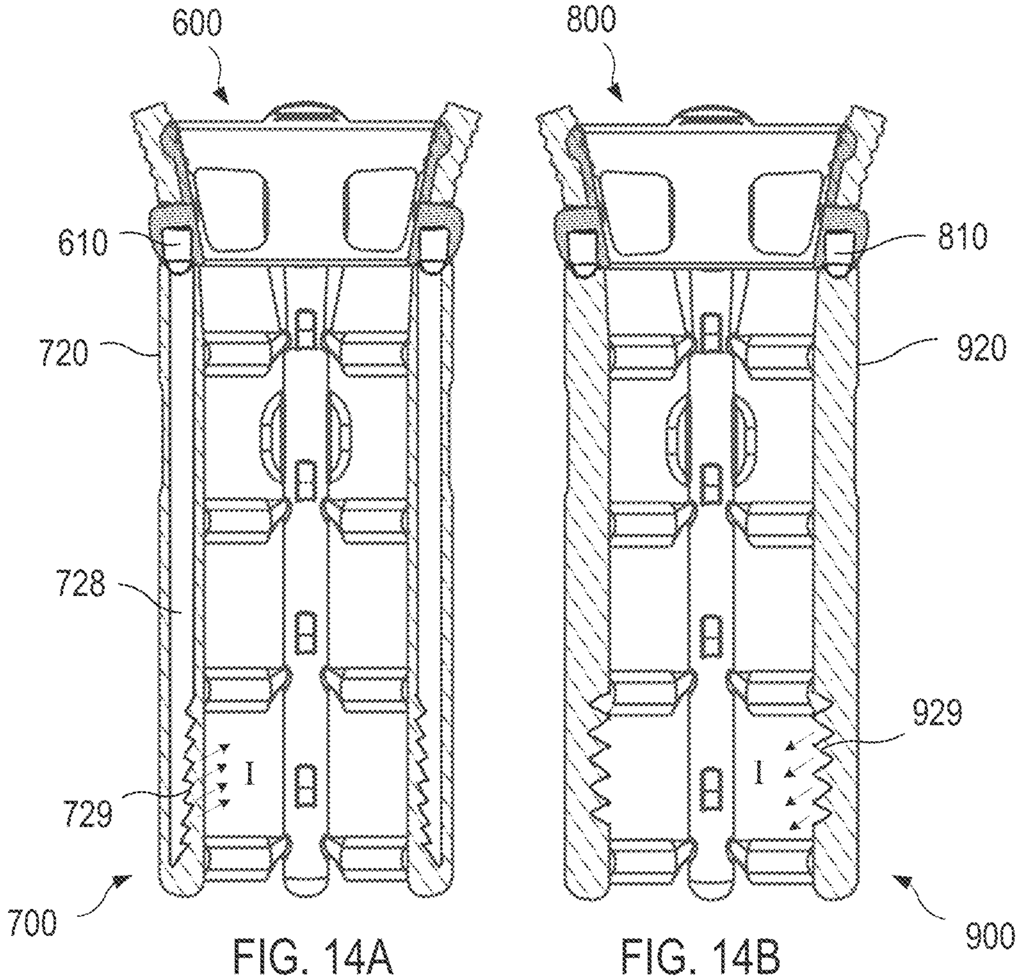
FIGS. 14A and 14B depict aspects of flutes and ring collars, according to embodiments of the present disclosure.

FIGS. 14A and 14B depicts aspects of an LED light ring collar with two different versions of a flute, according to embodiments of the present disclosure.

As shown in FIG. 14A, in some cases a ring collar 600 can include one or more light sources (e.g. an LED light source) 610 and one or more rods (e.g. 720) of the flute 700 can include one or more pieces of a clear rigid material or optical transmission mechanisms 728 which can transmit or carry light which is emitted from the light source. In some cases, the optical transmission mechanism can include an exit surface 729 through which light exits the optical transmission mechanism 728 (e.g. by dispersion, diffraction, or the like) so as to provide exiting light or illumination I within the flute 700.

As shown in FIG. 14B, in some cases a ring collar 800 can include one or more light sources (e.g. an LED light source) 810 and one or more rods (e.g. 920) of the flute 900 can operate to transmit or carry light which is emitted from the light source. In some cases, the rod can include an exit surface 929 through which light exits the optical transmission mechanism rod (e.g. by dispersion, diffraction, or the like) so as to provide exiting light or illumination I within the flute 900.

Figure 15A:
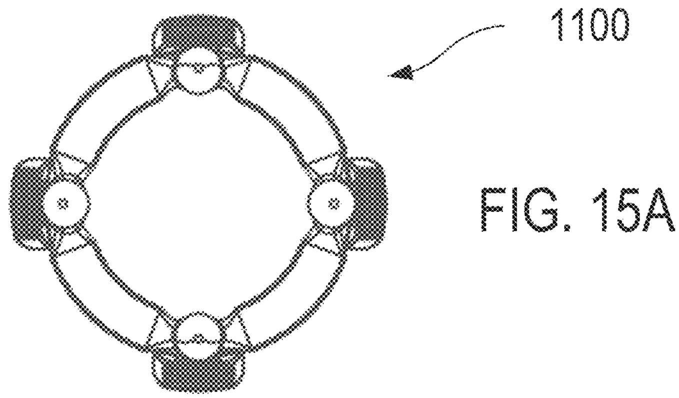
FIGS. 15A to 15C depict aspects of flutes, according to embodiments of the present disclosure.
Figure 15B:
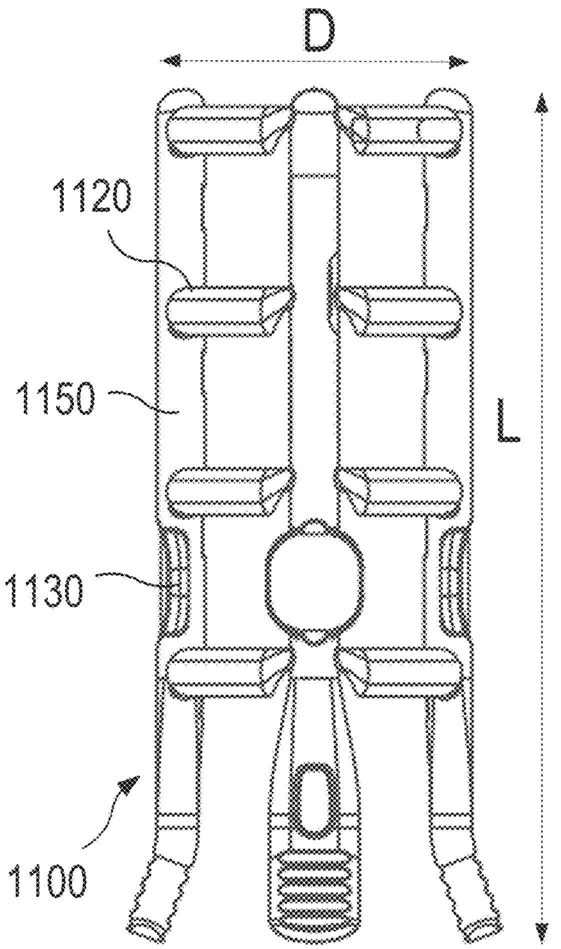
Figure 15C:
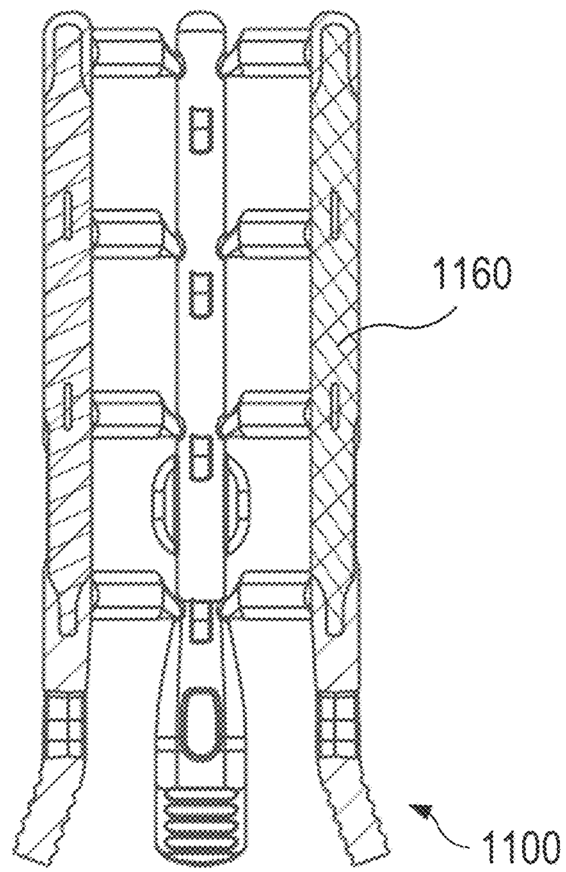

As shown in FIGS. 15A to 15C, a flute 1100 can have a working diameter D and working length L when in the unconstrained or expanded configuration. As illustrated in FIG. 15B, the flute 1100 can include one or more rods 1150, one or more rings 1120 engaged with the rods, and one or more padding mechanisms 1130 for engaging and/or supporting the introitus of the patient. In some cases, a padding mechanism 1130 can be coupled with a rod 1150 of the flute. In some cases, the working diameter D and working length L can determine the number of rings 1120 which may be needed or desired for construction of the flute. As shown in the cross-section view provided by FIG. 15C, in some cases the flute can have stiffening mechanisms 1160 such as stiffening rods engaged with or positioned within the rods 1150, so as to provide additional rigidity to the rods, thus enabling enhanced case of insertion into and removal from the patient. In some embodiments, a speculum flute can have a length of about 100 mm and a diameter of about 25 mm. In some embodiments, a speculum flute can have a length of about 75 mm and a diameter of about 20 mm. In some embodiments, a speculum flute can have a length of about 125 mm and a diameter of about 30 mm. In some embodiments, a speculum flute can have a length of about 150 mm and a diameter of about 35 mm. Other lengths and/or diameters are contemplated by embodiments of the present disclosure.

As shown in FIGS. 16A to 16C, a handle 200 can include a proximal section 210, a distal section 220, and a medial section 230. Proximal section 210 includes proximal extrusions 202, 204 which as discussed elsewhere herein are configured to engage prong slots of a flute. Medial section 230 includes medial extrusions 217, 219 which as discussed elsewhere herein are configured to engage prong slots of a flute. Distal section 220 includes external gripping mechanisms 251, 252, 253, 254, 255, and 256. Distal section 212 also includes grooves 201, 203 (e.g. configured to at least partially receive nesting rods 324, 328, respectively).

With reference to FIG. 10B, it can be understood that speculum 400 includes a handle 1000 and a flute 300 that can be loaded onto the handle 1000. Additional aspects of the handle 1000 can be further understood with reference to FIGS. 17A to 17C. As shown in FIG. 10B, handle 1000 can include a proximal section 1210, a distal section 1220, and a medial section 1230 disposed between the proximal section 1210 and the distal section 1220. The flute 300 (with additional reference to FIGS. 10A, 10C, 11B, and 11C) can include one or more rings (e.g. rings 312, 314, 316, and 316) which so as to define or provide a tunnel 310 into which at least a portion of the handle 1000 may be placed. The rings of the flute 300 can be supported by one or more rods, and each rod can include a proximal prong. For example, rod 322 includes proximal prong 321 and rod 324 includes proximal prong 323. This embodiment includes two additional rods having proximal prong 325 and proximal prong 327 respectively. In some embodiments, one or more rings of a flute can include one or more stiffening elements or supports. In some cases, such stiffening elements or supports can be over molded or exposed. In some cases, such a stiffening element or support can be disposed internally at least partially within a ring. As discussed elsewhere herein, one or more rods can include one or more stiffening elements or supports as well, and such rod stiffening elements or supports can be over molded or exposed. Exemplary ring stiffening elements or supports can be made of an elastic metal such as nitinol. A ring stiffening element or support can be configured to flex or bend in the same or similar manner in which a ring would flex, for example as ring 311 is shown bending or flexing in FIG. 12. In some cases, a ring stiffening element can be coupled with prongs of a flute, for example as discussed elsewhere herein with reference to FIG. 20.

The handle 1000 can include one or more extrusions or other connection mechanisms by which one or more rods of the flute 300 can be mechanically coupled with the handle 1000. For example, handle 1000 can include one or more proximal extrusions (e.g. 1202 as depicted in FIGS. 17A to 17C) which can engage or be mechanically coupled with one or more prong slots, respectively. With reference to FIG. 10B, it can be seen, for example, that slot 321A of prong 321 can be placed to engage extrusion 1202 of handle 1000. Likewise, slot 325A of prong 325 can be placed to engage extrusion 1204 of handle 1000.

With the prong slots 321A, 325A and corresponding handle proximal extrusions 1202, 1204 engaged with one another, the handle 1000 can be retracted proximally relative to the flute 300, thereby drawing prongs 321 and 325 of the flute in a relatively proximal direction as well. As a result, the rings 312, 314, 316, 318 of the flute become folded, as rod 322 and the rod 326 (which is laterally opposed from rod 322) are pulled proximally relative to rods 324 and 328, as shown in FIG. 11B. As discussed elsewhere herein, in some cases rods 324 and 328 can be referred to as nesting rods, as they can be positioned to nest at least partially within respective grooves of the handle. With reference to FIGS. 10B, 11B, 11C, and 17CB in combination, it can be seen that when retracting rods 322, 326 are drawn proximally, nesting rod 324 can be at least partially positioned within groove 1201, and nesting rod 328 can be at least partially positioned within groove (hidden) opposing groove 1201.

With returning reference to FIG. 11C, it can be seen that a folding action can reduce the profile of the rings. To help hold the rings in a folded configuration, internal gripping features of the handle can be engaged with the nesting rods. As shown in FIG. 17C, handle 1000 includes a plurality of internal gripping mechanisms 1251, 1252, 1253, 1254. In some cases, an internal gripping mechanism can be provided as a pin, an extrusion, a post, or the like.

After handle 1000 is moved in a proximal direction relative to the flute (which also moves rod 322 in the proximal direction), internal gripping mechanisms 1251, 1252, 1253, 1254 can be engaged with corresponding engagement mechanisms such as apertures or the like (not shown) of nesting rod 324. Likewise, internal gripping mechanisms on the opposing side of handle 1000 can be engaged with engagement mechanisms on nesting rod 328. Hence, it can be understood that handle 1000 can include grooves or recesses that are configured to accept or engage nesting rods when the rings are folded. For example, as rings are folded when handle 1000 is drawn proximally, nesting rod 324 can be positioned at least partially within groove 1201.

Once the internal gripping mechanisms have been engaged with the rods, the handle effectively operates to hold the rings in the folded orientation, and thus the flute is maintained in a low profile, contracted, or constrained configuration (e.g. as shown in FIG. 11B). While in this low profile or constrained configuration, the flute can be inserted into the patient. Once positioned as desired within the patient, the handle can be disengaged from the flute, for example with reference to FIG. 17C by moving slider or sliding mechanism 1005 forward or in the distal direction as indicated by arrow A, thus also moving the extrusions 1202, 1204 in the distal direction as well, and thereby relaxing or removing the folding forces applied to the rings. Flute prongs can then be disengaged from the handle 1000. According to some embodiments, the rings can be manufactured or provided so that they are biased toward an unfolded configuration, such that when the folding forces which were previously applied to the rings are subsequently removed, the rings return to their unfolded orientation, thus allowing the flute to return to an expanded or unconstrained configuration (e.g. as shown in FIG. 10B). In some cases, handle 1000 can include one or more railings 1203 that can assist with disassembly of the speculum. In some cases, a railing (e.g. 1203) can act as a protrusion that interferes and/or pushes the rods off of the handle's flute prongs by moving slider 1005 forward or in the distal direction as indicated by arrow A. This can improve accessibility of detaching the speculum or flute from the handle.

Figure 18A:
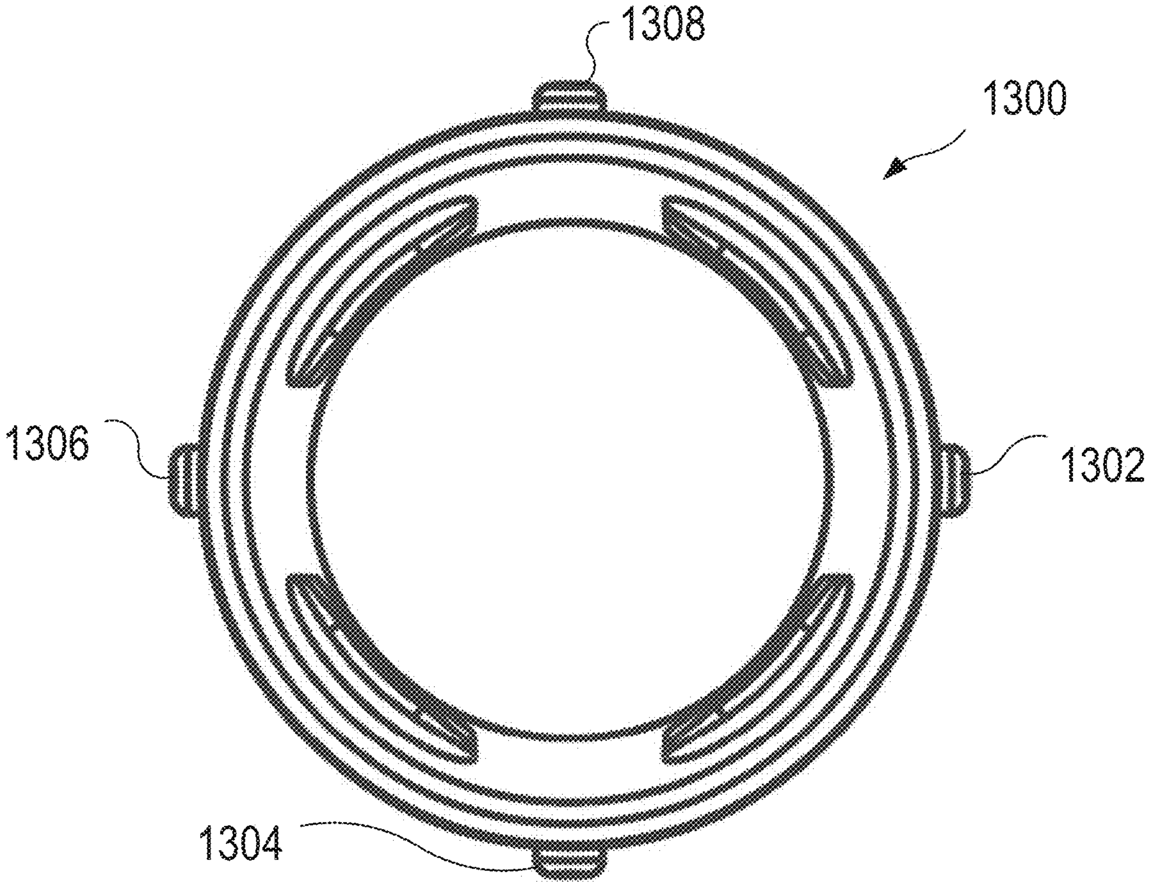
FIGS. 18A and 18B depict aspects of a ring collar, according to embodiments of the present disclosure.
Figure 18B:
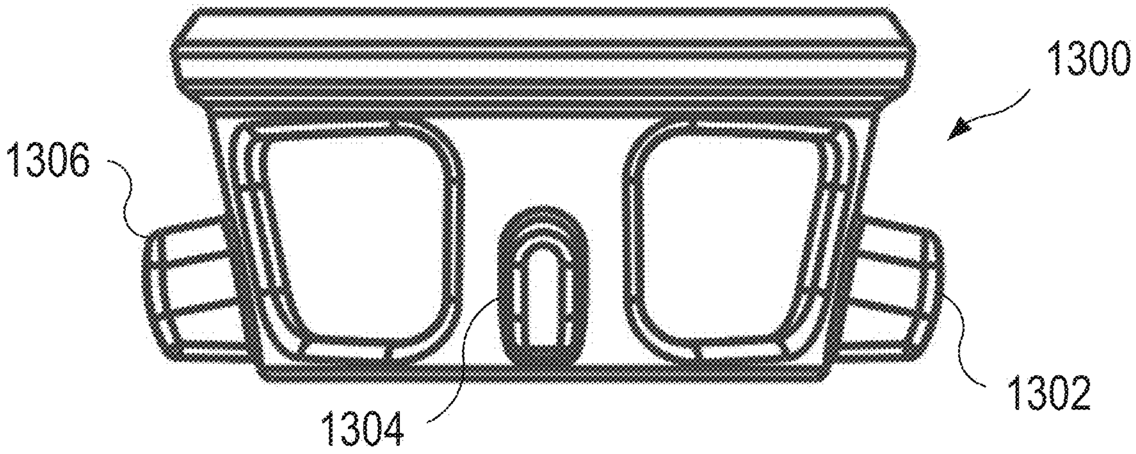

FIGS. 18A and 18B depict aspects of a ring collar 1300, according to embodiments of the present disclosure. In some cases, the ring collar 1300 can include one or more tabs (e.g. 1302, 1304, 1306, 1308) configured to engage respective prong slots of a flute. When the ring collar 1300 is engaged with the flute, it operates to hold the flute in the expanded configuration and the rings in the unfolded orientation, even when compressive forces are applied against the flute.

Figure 19A:
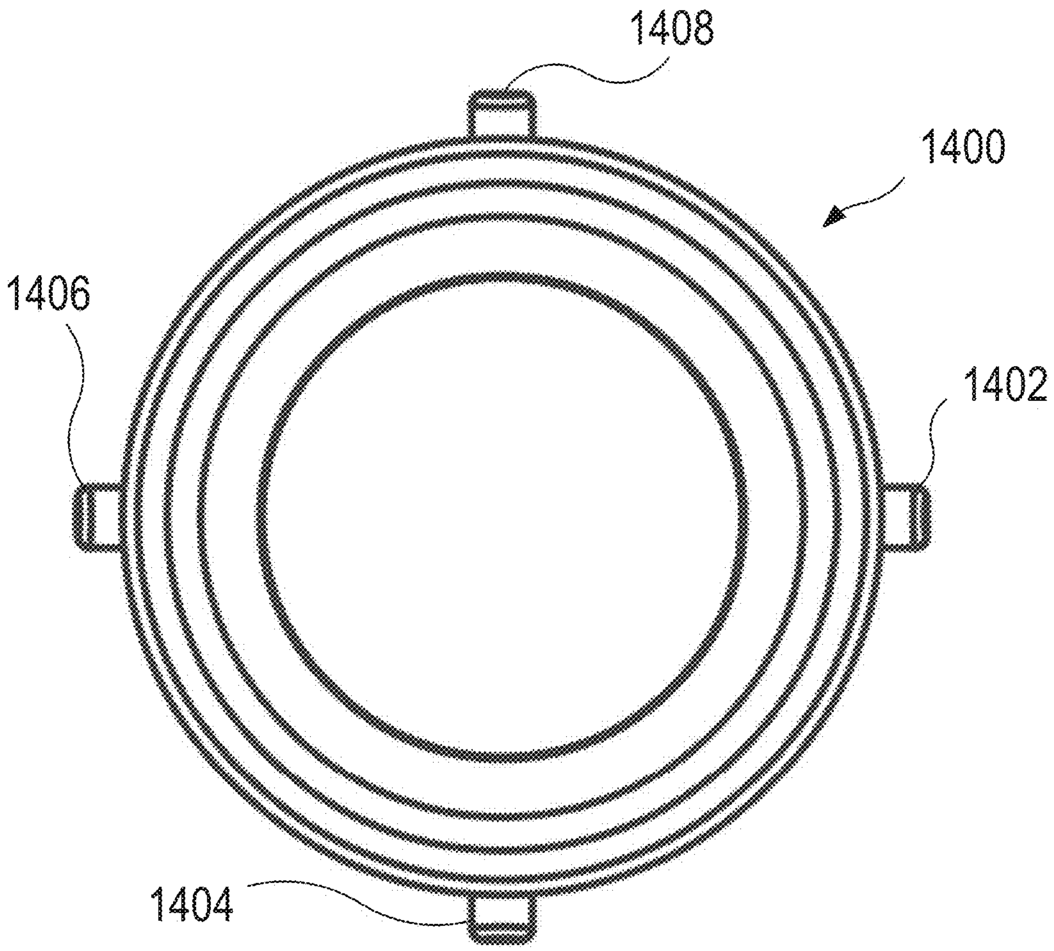
FIGS. 19A and 19B depict aspects of a ring collar, according to embodiments of the present disclosure.
Figure 19B:
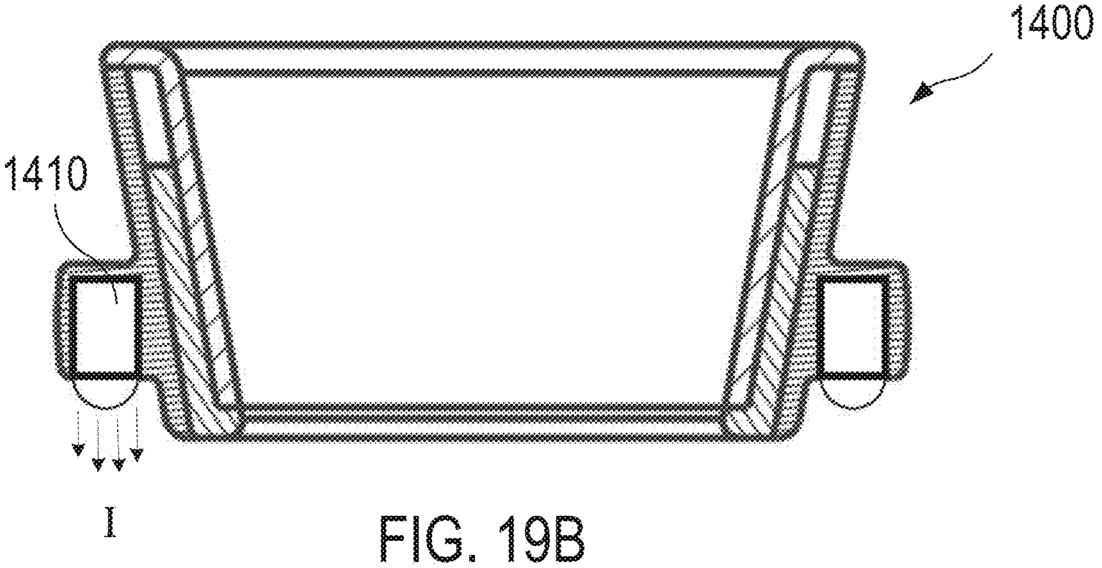

FIGS. 19A and 19B depict aspects of a ring collar 1400, according to embodiments of the present disclosure. In some cases, the ring collar 1400 can include one or more tabs (e.g. 1402, 1404, 1406, 1408) configured to engage respective prong slots of a flute. When the ring collar 1400 is engaged with the flute, it operates to hold the flute in the expanded configuration and the rings in the unfolded orientation, even when compressive forces are applied against the flute. As shown here, a ring collar 1400 can also include one or more light sources 1410 (e.g. an LED light source). Such light sources 1410 can operate to provide light I to the interior of a speculum flute.

Figure 20:
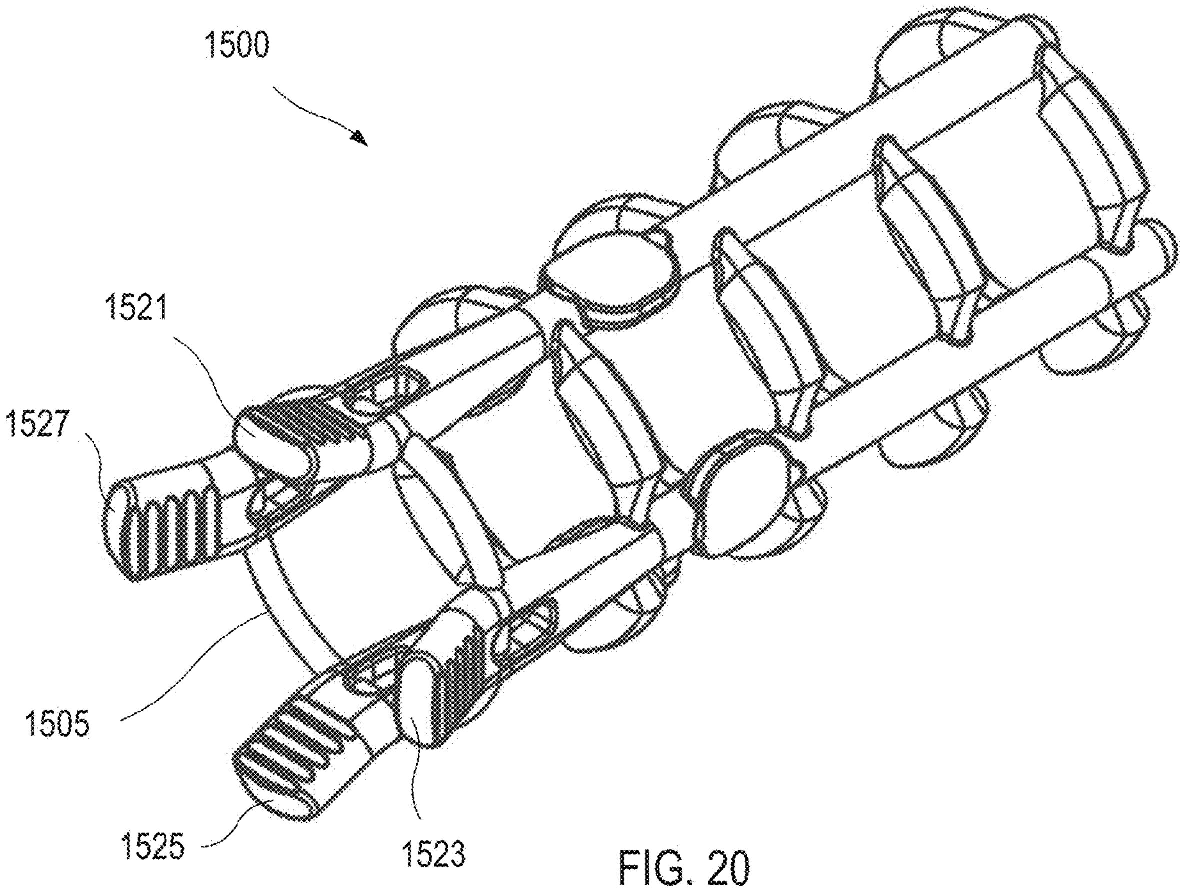
FIG. 20 depicts aspects of a flute, according to embodiments of the present disclosure.
Figure 21A:
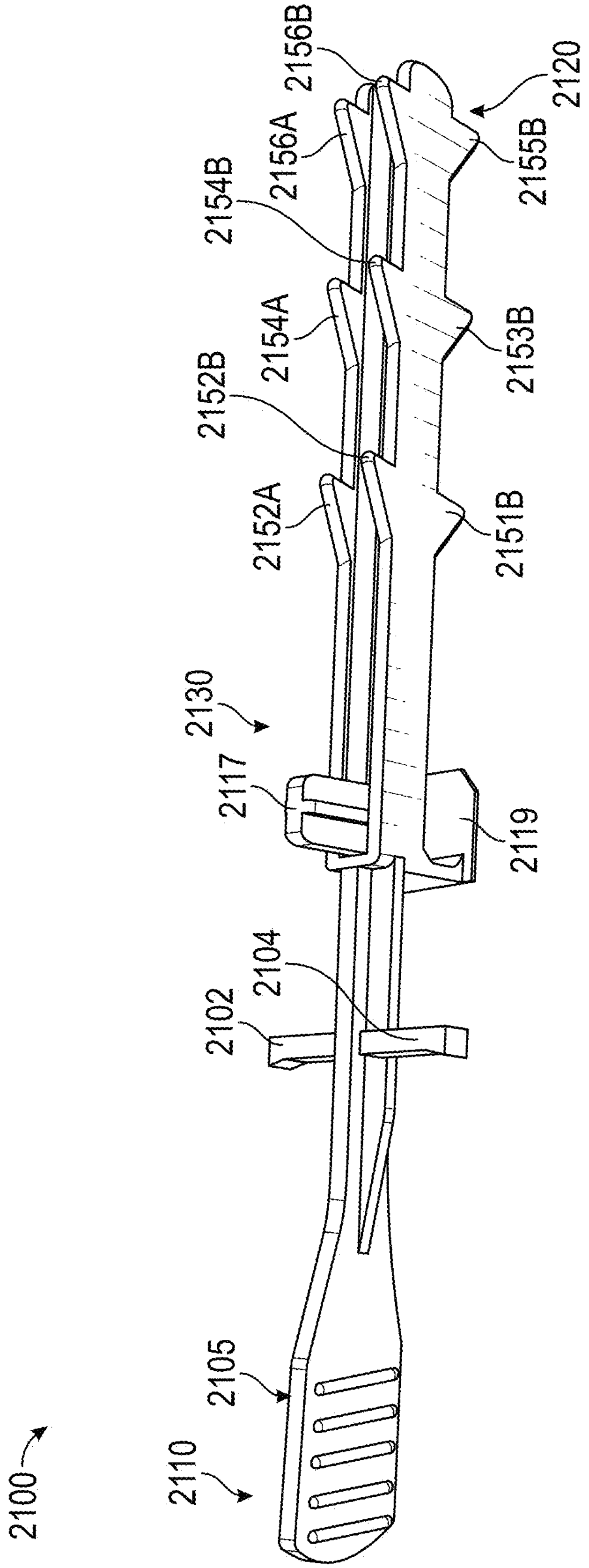
FIGS. 21A to 21E depict an introducer for opening/closing a speculum between collapsed and expanded positions.
Figure 21B:
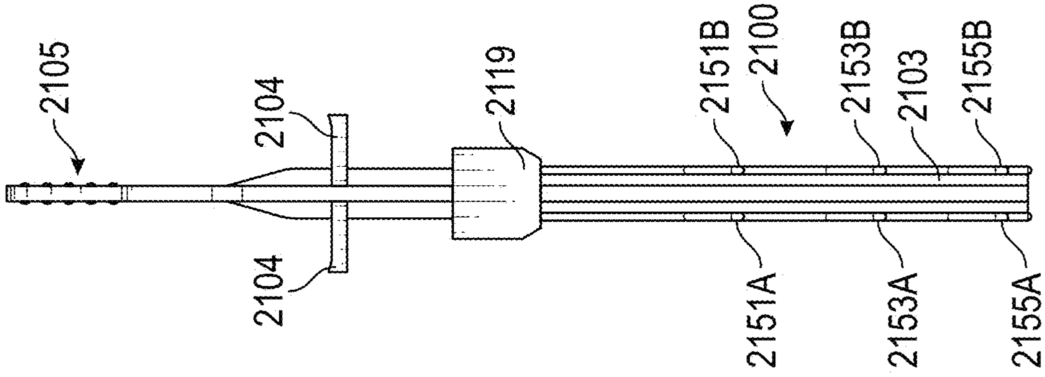
Figure 21C:
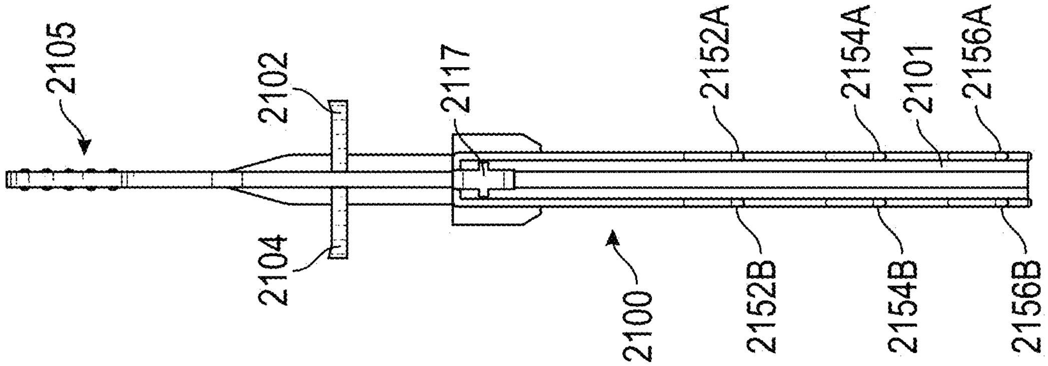
Figure 21D:
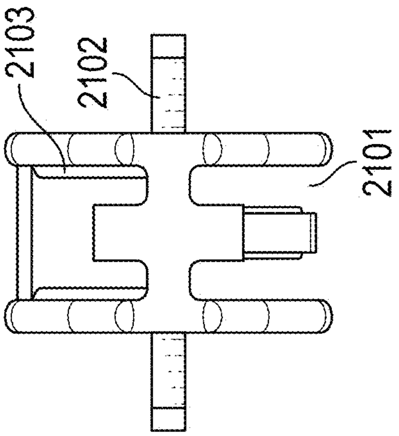
Figure 21E:
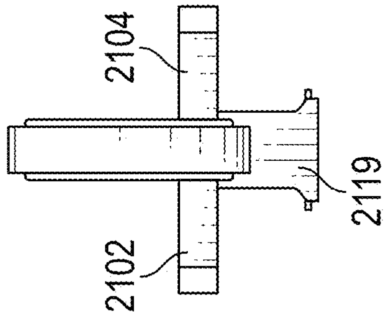

FIG. 20 depict aspects of a flute 1500 according to embodiments of the present disclosure. As shown here, flute includes a proximal ring stiffening element 1505 that is coupled with one or more proximal prongs (e.g. 1521, 1523, 1525, 1527) of the flute. In some cases, a proximal ring stiffening element can be provided as a flexible component such as a flexible metal component, and can operate to provide additional stiffness and improved retention of a flute or speculum in an expanded state. In some embodiments, a proximal ring stiffening element can be configured to bend or flex in the same or similar manner in which a ring would bend or flex, for example as ring 311 is shown bending or flexing in FIG. 12. In some cases, a proximal ring stiffening element 1505 can be provided as a wire, or as multiple wires, or as multiple wires wound or braided together.

Figure 22:
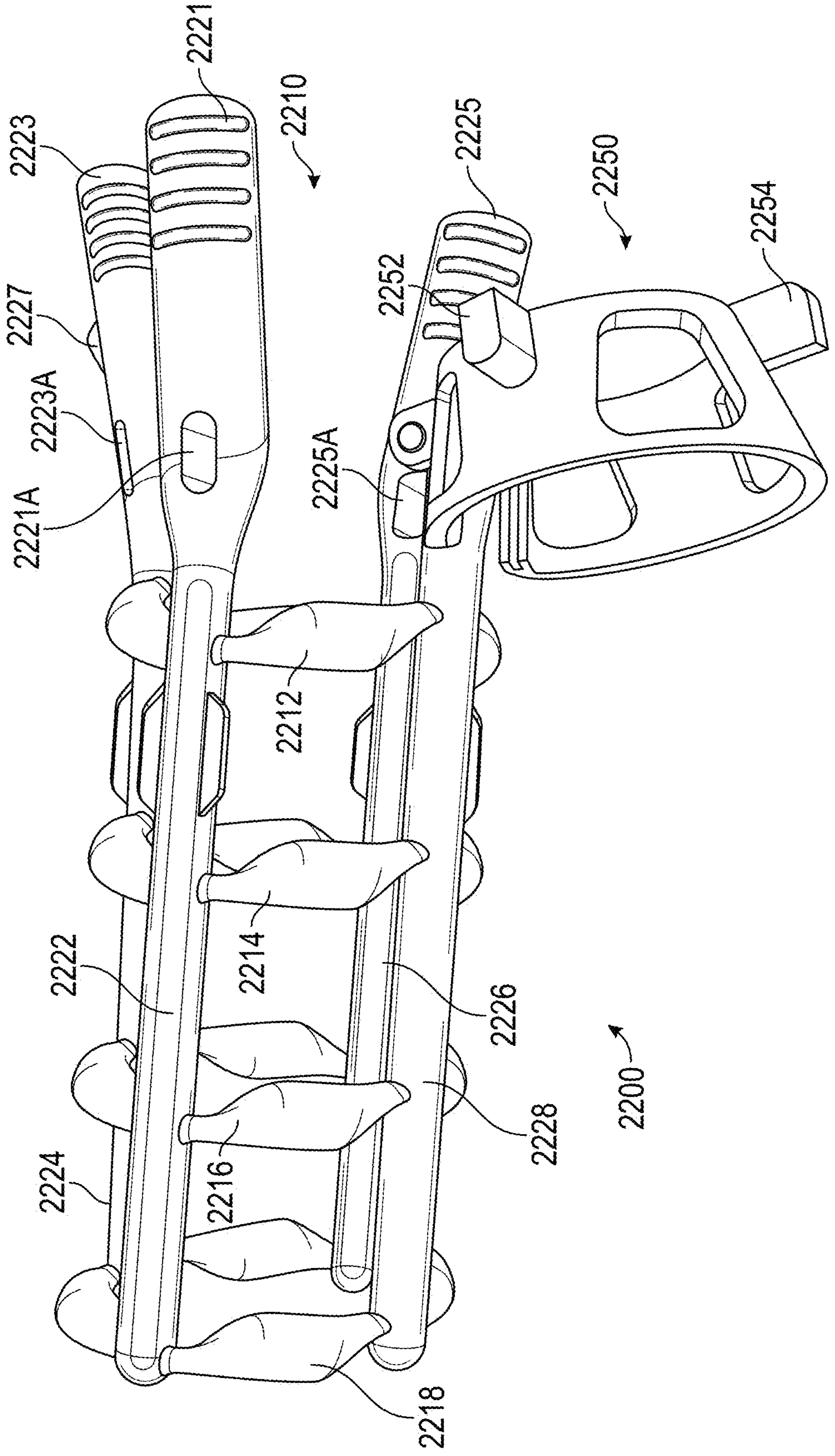
FIG. 22 depicts an expanded speculum with collar in an unlocked position.
Figure 23:
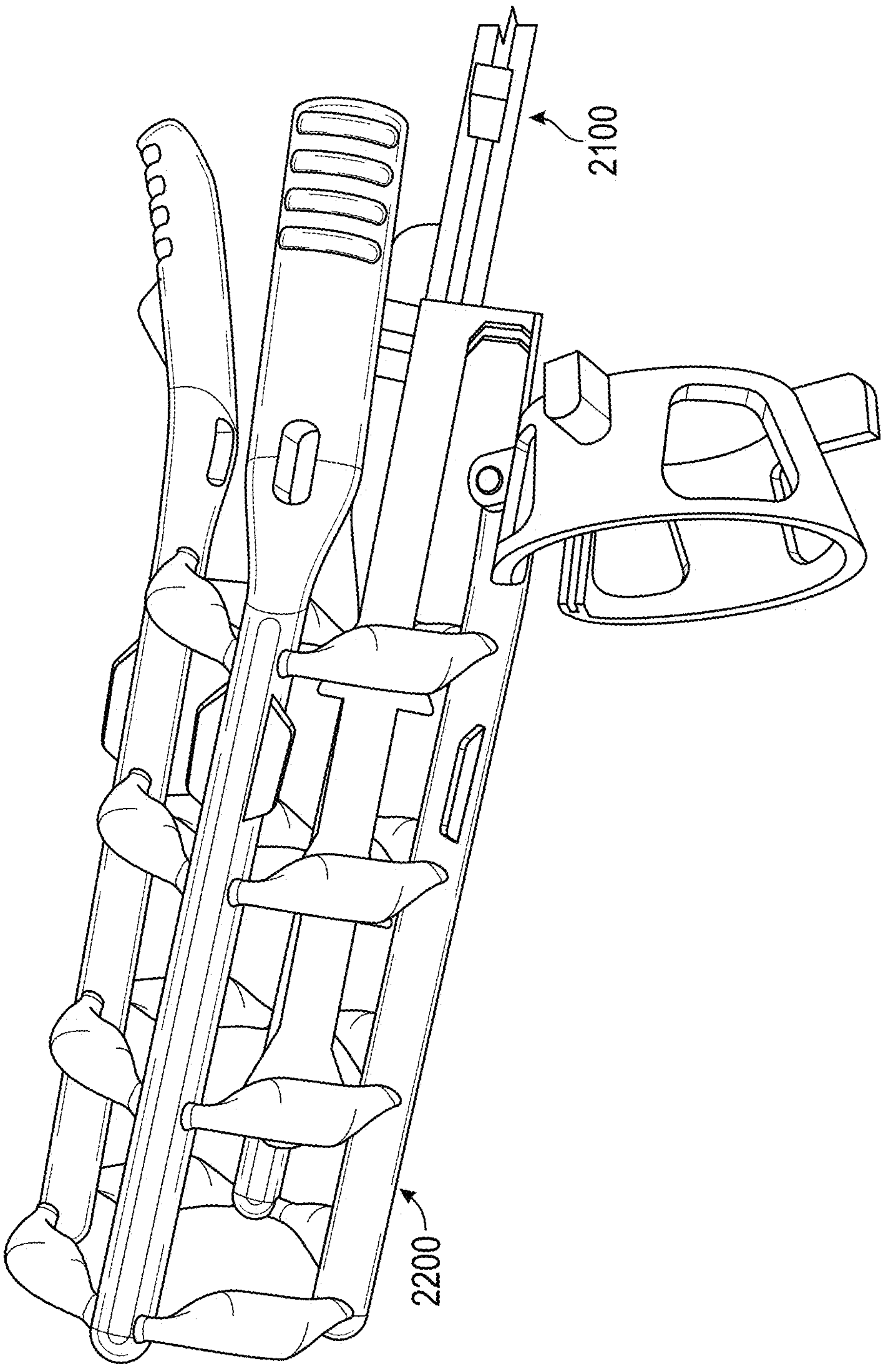
FIG. 23 depicts the speculum of FIG. 22 with the introducer of FIGS. 21A to 21E insert in an interior portion of the speculum.
Figure 24:
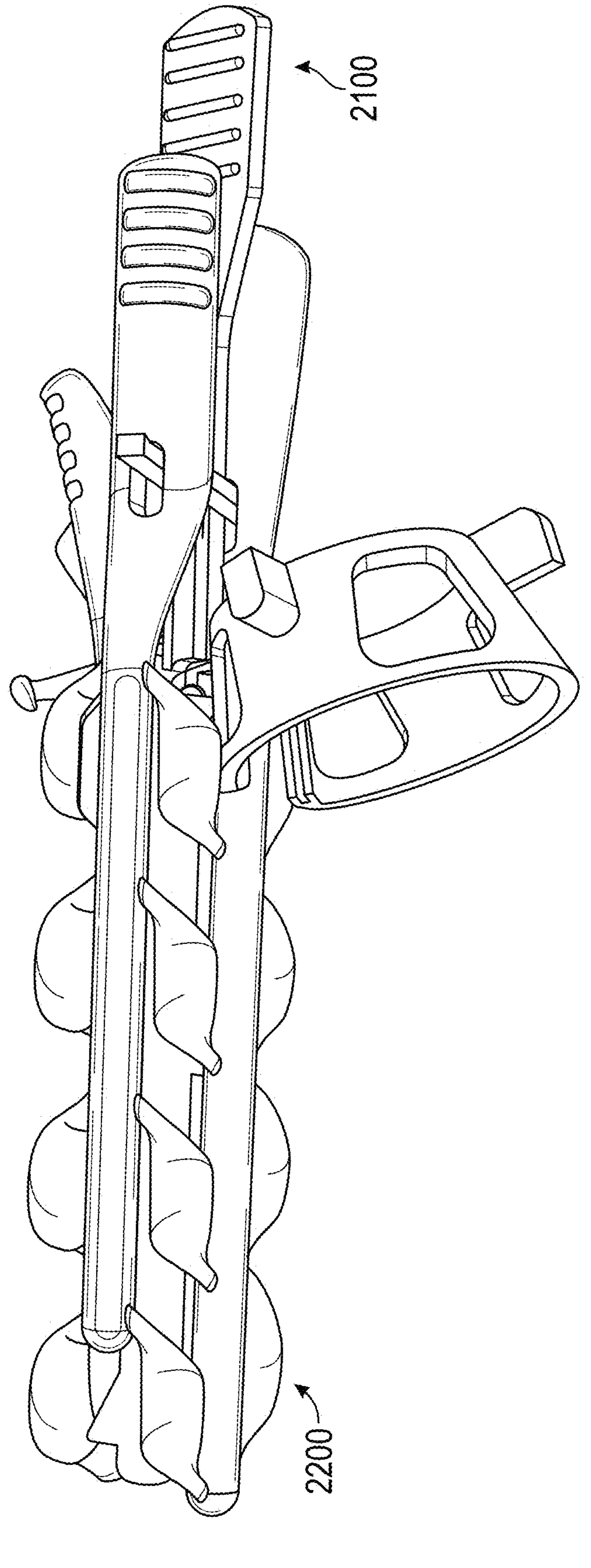
FIG. 24 depicts the speculum of FIG. 23 and introducer of FIGS. 21A to 21E in a collapsed position for insertion into or removal therefrom a vagina.
Figure 25A:
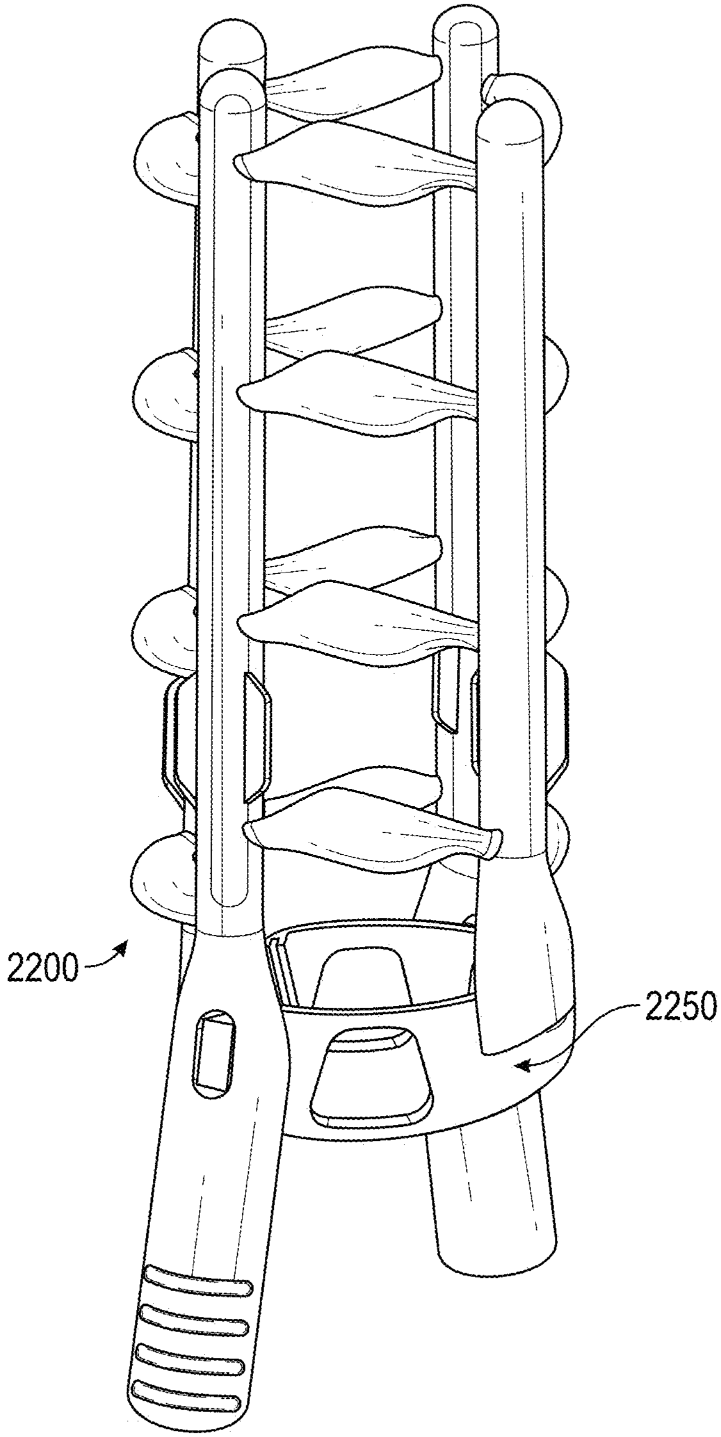
FIGS. 25A to 25G depict the speculum of FIG. 24 in an expanded position with the introducer removed and with a collar disposed in position to retain the speculum in the expanded position.
Figure 25B:
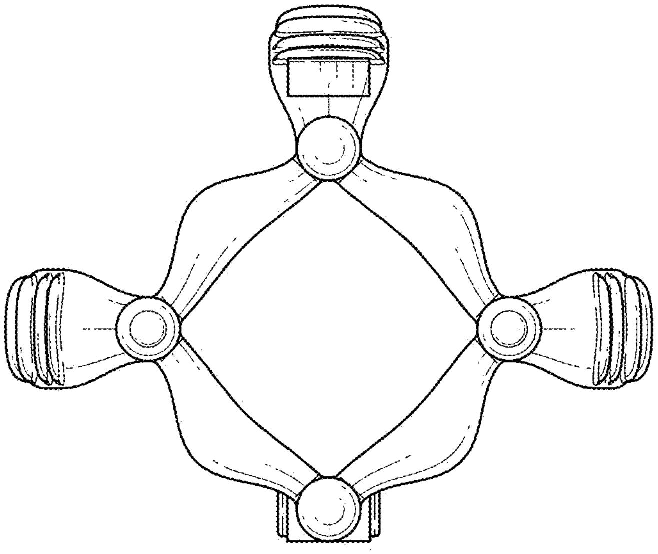
Figure 25C:
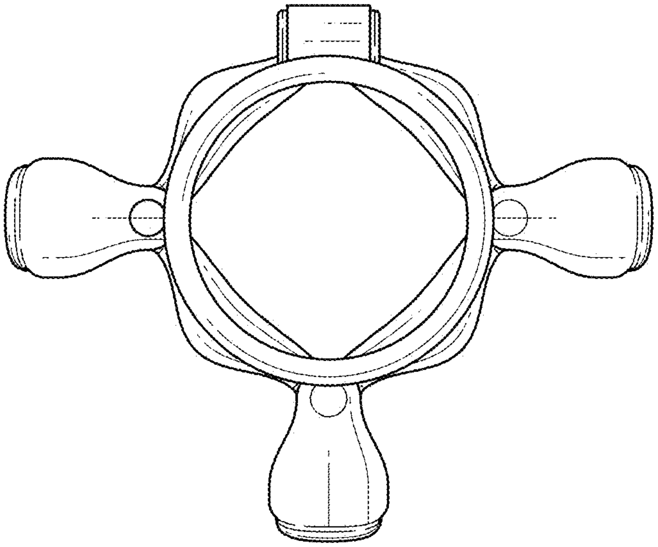
Figure 25D:
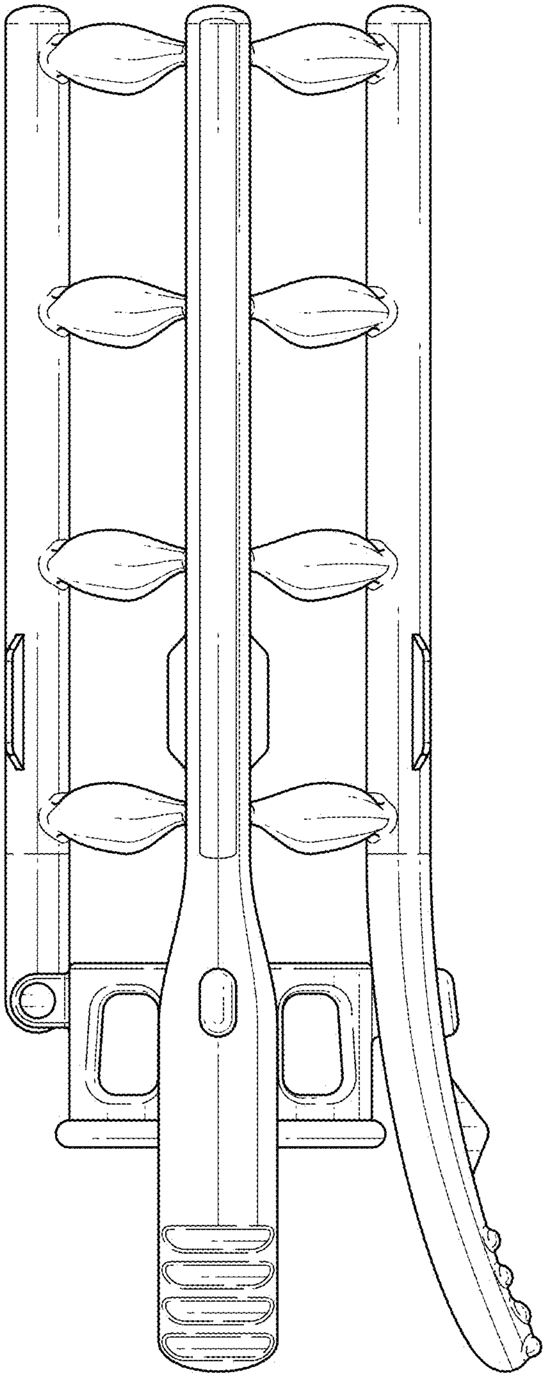
Figure 25E:
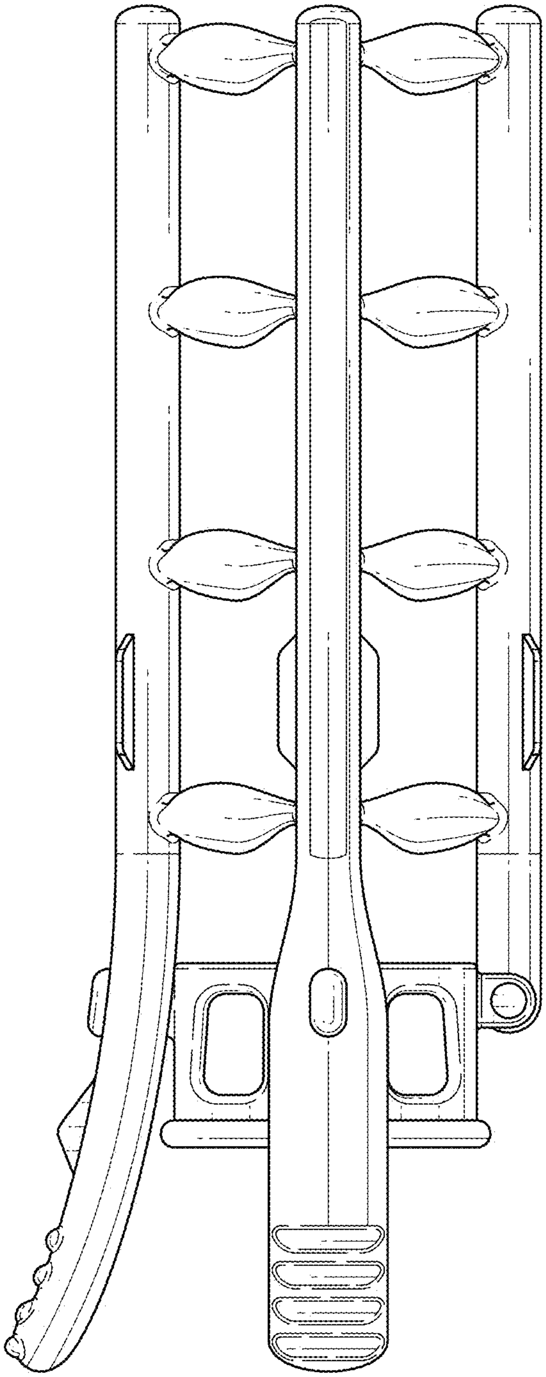
Figure 25F:
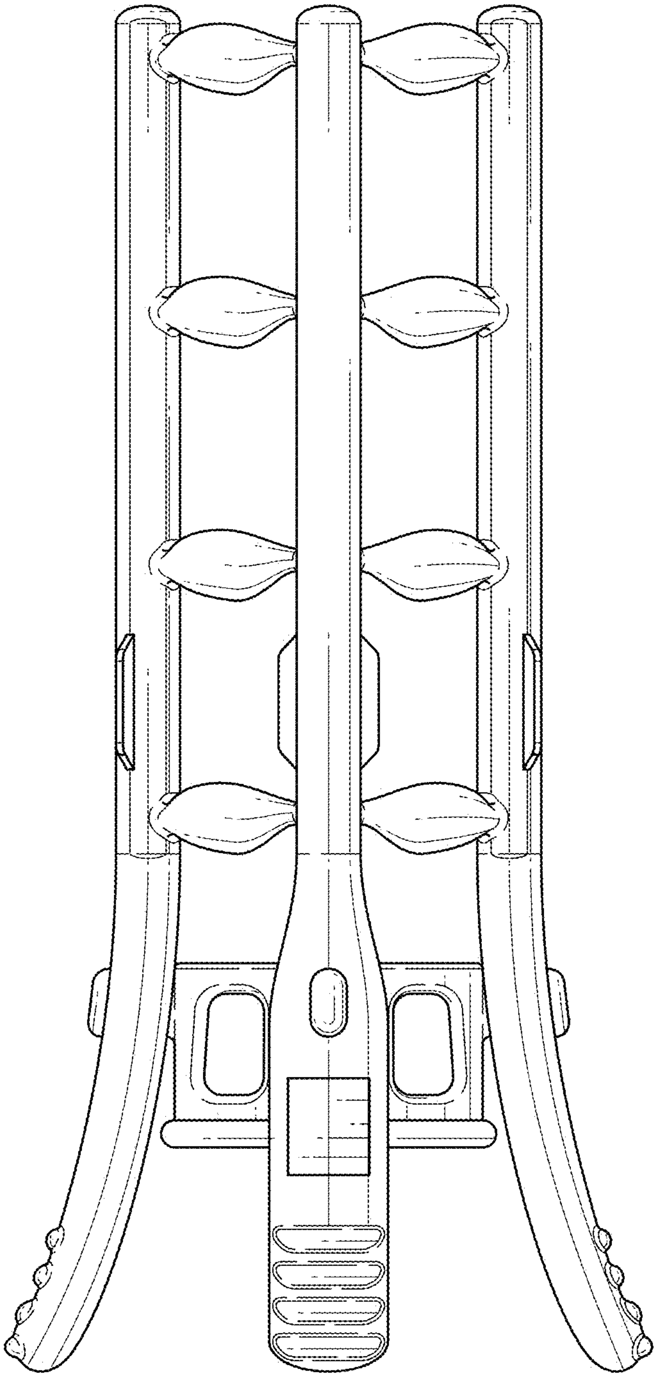
Figure 25G:
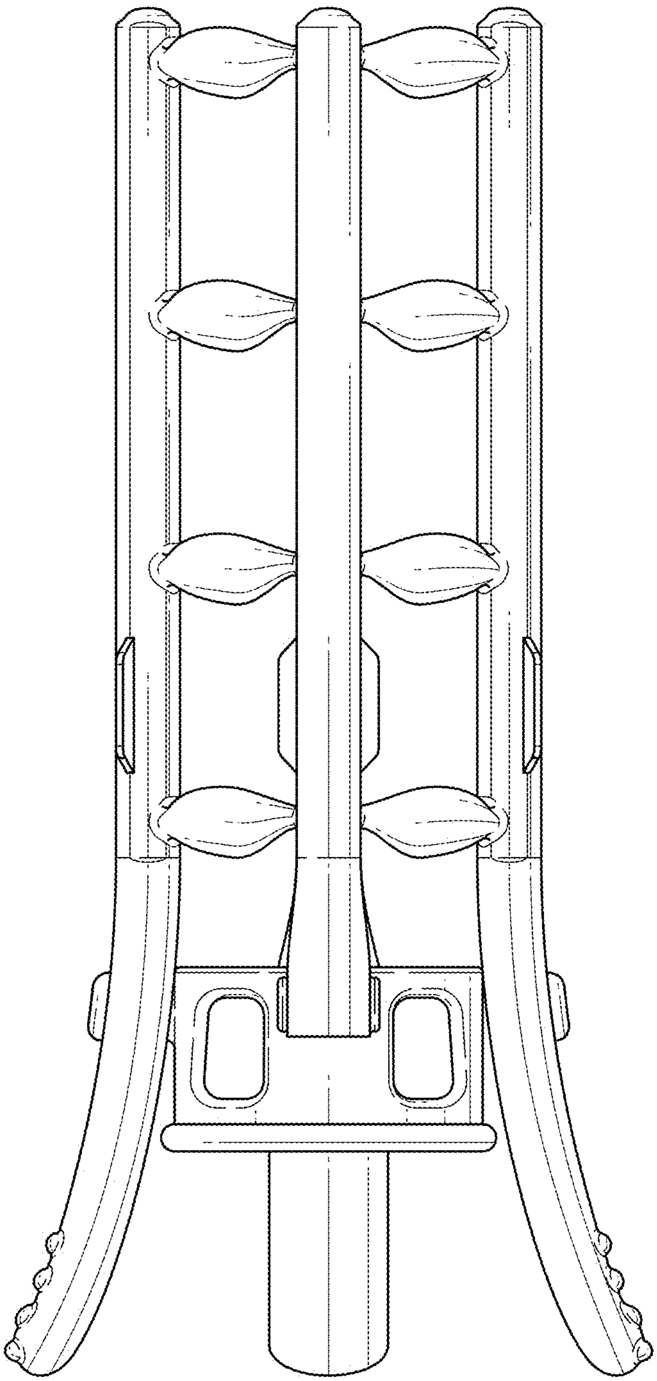
Figure 26:
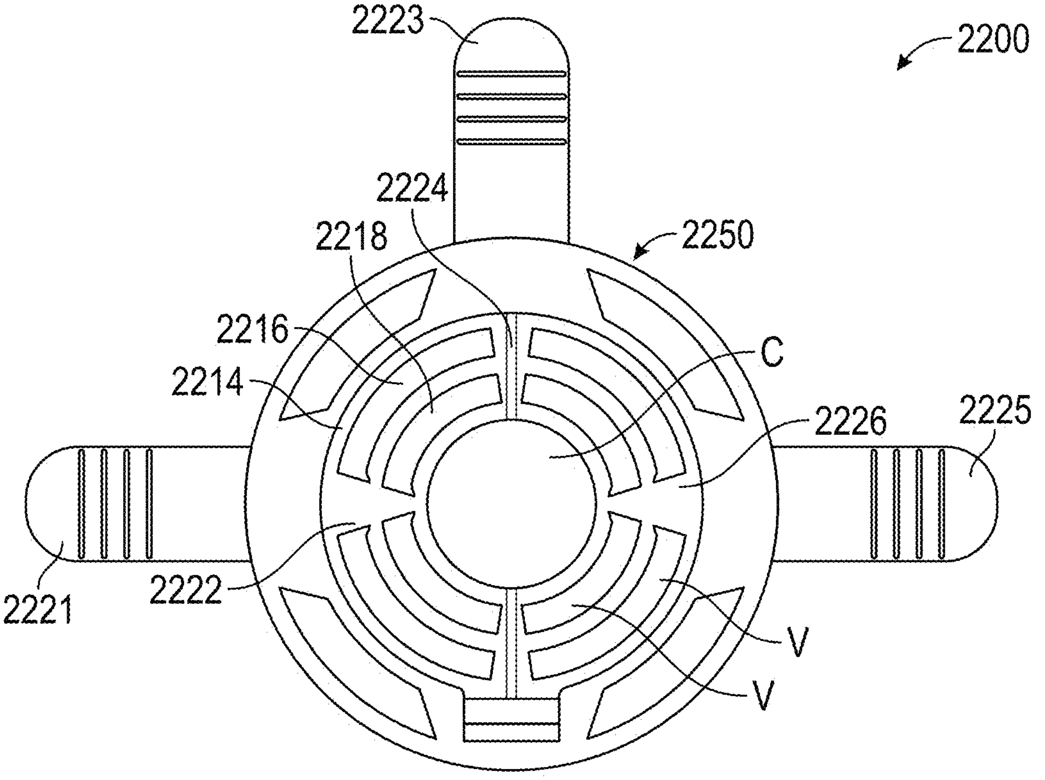
FIG. 26 depicts an interior view of the expanded speculum of FIGS. 25A to 25G disposed in a vagina.
Figure 27:
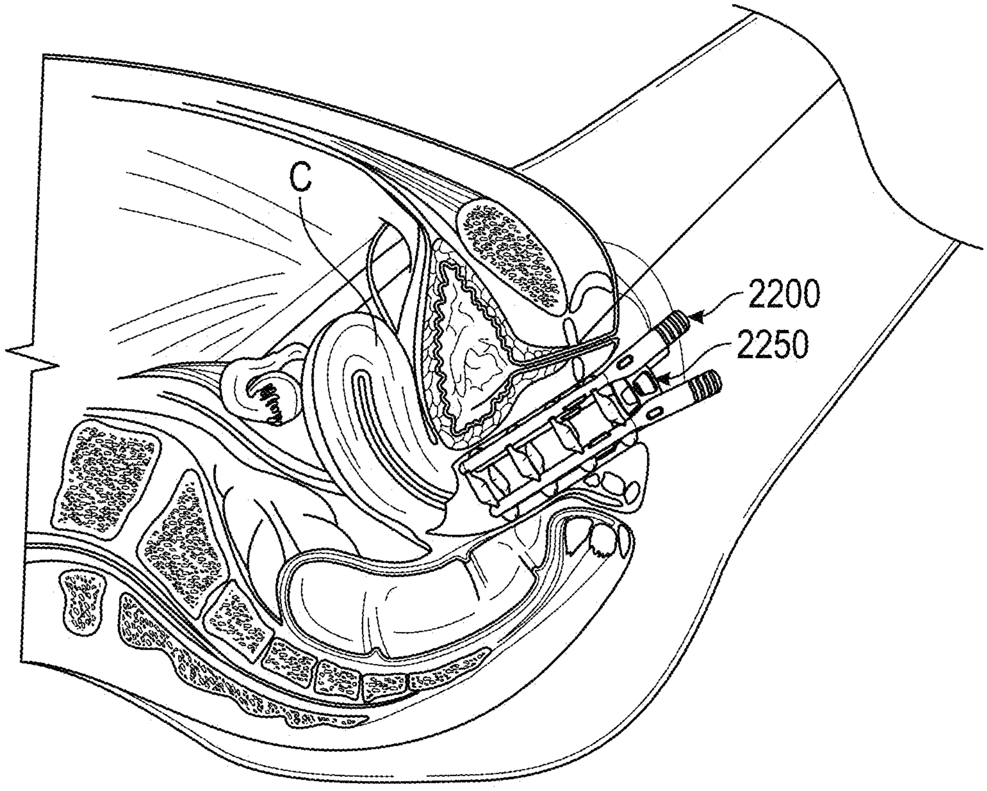
FIG. 27 depicts a perspective view of the expanded speculum of FIG. 25 disposed in a vagina.
Figures 28A, 28B, 28C, 28D, 28E, 28F:
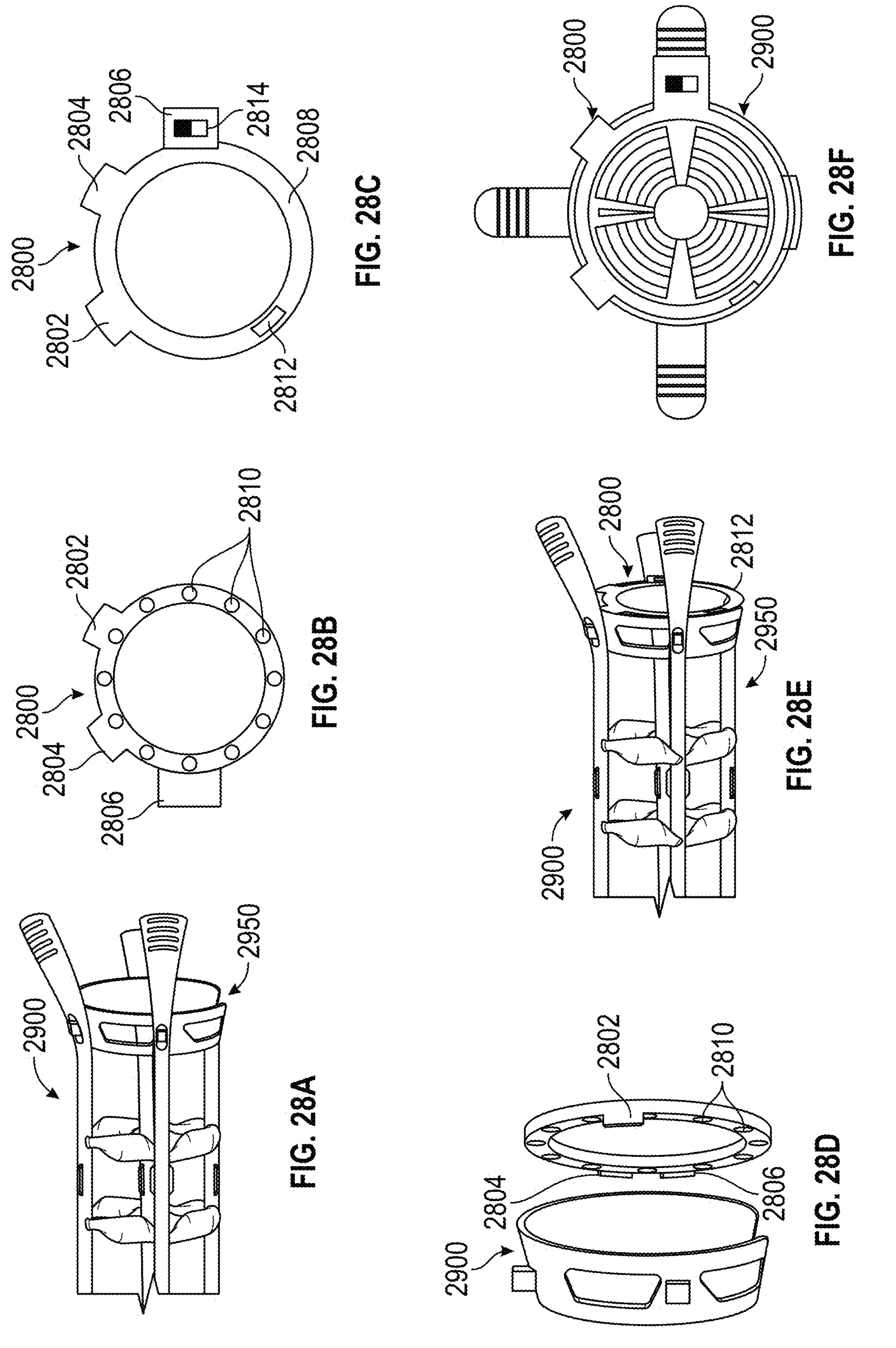
FIG. 28A to 28F depict aspects of a light for an exemplary speculum.

FIGS. 21A to 21E depict an introducer for opening/closing a speculum between collapsed and expanded positions. FIG. 22 depicts an expanded speculum with collar in an unlocked position. FIG. 23 depicts the speculum of FIG. 22 with the introducer of FIGS. 21A to 21E insert in an interior portion of the speculum. FIG. 24 depicts the speculum of FIG. 23 and introducer of FIGS. 21A to 21E in a collapsed position for insertion into or removal therefrom a vagina. FIGS. 25A to 25E depicts the speculum of FIG. 24 in an expanded position with the introducer removed and with a collar disposed in position to retain the speculum in the expanded position. FIG. 26 depicts an interior view of the expanded speculum of FIG. 25 disposed in a vagina. FIG. 27 depicts a perspective view of the expanded speculum of FIG. 25 disposed in a vagina. FIG. 28A to 28F depict aspects of a light for an exemplary speculum.

FIGS. 21-28F show additional aspects of embodiments of a speculum(s). The embodiments shown in FIGS. 21-28F are exemplary and can include features detailed in other embodiments in this disclosure even if not shown in the associated drawings.

In at least one aspect, FIGS. 21-28F include an expander with areas that extend out to allow traction for rings to collapse/fold down along the expander as it is attached to a collar along, at, or by a small catch. The collar can be attached to the flute by a small axis point along the side of the flute. The distal end of that part of the flute can be removed to allow the collar the ability to rotate/swivel on an axis, such as upward, once the expander is removed. The collar can remain attached to, along, or at the three remaining distal ends of the flute at the small cut-out locations already in the flute.

The introducer 2100 shown in FIGS. 21A to 21E are similar to the handle 200 detailed above. However, the introducer 2100 shown in FIGS. 21A to 21E can include a proximal section 2110, a distal section 2120, and a medial section 2130. Proximal section 2110 includes grip portion 2105 and proximal extrusions or side prongs 2102, 2104 which are configured to engage prong slots of a flute. Medial section 2130 includes medial extrusions 2117, 2119 which are configured to engage prong slots of a flute. In some embodiments, extrusion 2117 is referred to as an anterior prong and extrusion 2119 is referred to as a saddle. Distal section 2120 includes external gripping mechanisms or petals 2151, 2152, 2153, 2154, 2155, and 2156. Distal section 2120 also includes grooves 2101, 2103 (e.g. configured to at least partially receive nesting rods). The grooves 2101 and 2103 are generally disposed adjacent or on a sliding tract.

FIG. 22 depicts aspects of a speculum 2200 according to embodiments of the present disclosure. As shown, speculum 2200 is similar to flute 1500 of FIG. 20 but includes a collar 2250 attached to the speculum 2200 in place of one prong. The speculum 2200 can include one or more rings (e.g. rings 2212, 2214, 2216, and 2218) which so as to define or provide a tunnel 2210 into which at least a portion of the introducer 2100 may be placed. The rings of the speculum 2200 can be supported by one or more rods, and each rod can include a proximal prong. For example, rod 2222 includes proximal prong 2221, rod 2224 includes proximal prong 2223, and rod 2226 include proximal prong 2225. The collar 2250 is similar to ring collar 1300 detailed in FIGS. 18A and 18B and similar to ring collar 1400 detailed in FIGS. 19A and 19B, however collar 2250 is attached to speculum 2200 along rod 2228 in a position to be moved from a disengaged position as shown in FIG. 22 to an engaged or locked position as shown in FIGS. 25, 26, 27, 28A, 28E, and 28F. The collar 2250 can include tabs 2252, 2254, 2256 configured to engage respective prong slots 2221A, 2223A, and 2225A, respectively. When the collar 2250 is engaged with the speculum, it operates to hold the speculum 2200 in the expanded configuration and the rings in the unfolded orientation, even when compressive forces are applied against the speculum 2200. In some cases, a speculum can include one or more padding mechanisms or introitus pads, and such padding mechanism can be coupled with or disposed on the speculum. In exemplary embodiments, a padding mechanism includes or is made of a compressible material, can operate to support and/or engage the vaginal introitus of a patient, and a physician or other health provider can use one or more of the padding mechanisms as a depth indicator or depth control mechanism, whereby the action of lining up the padding mechanisms with the introitus of the patient can ensure that the flute is inserted into the vagina at the desired or appropriate depth. In some cases, a padding mechanism can be coupled with a rod of the speculum. In some cases, each individual rod of a speculum includes or is coupled with a corresponding individual introitus pad. In some cases, a speculum or at least one rod includes a circumferential protrusion or padding mechanism configured to support and/or engage the introitus.

Prong 2223 of rod 2224 is shown with a bump or other raised surface 2227 that is provided to allow leverage against providers finger to use, for example, when collapsing the device back down to remove the speculum. The bump 2227 is generally created out of the same material as the speculum, for example, silicone, and can be provided on any of prongs 2221, 2223, or 2225, or on multiple prongs.

FIG. 23 depicts the speculum 2200 of FIG. 22 with the introducer 2100 of FIGS. 21A to 21E insert in an interior portion of the speculum 2200. FIG. 24 depicts the speculum of FIG. 23 and introducer of FIGS. 21A to 21E in a collapsed position for insertion into or removal therefrom a vagina. FIGS. 25A to 25G depict the speculum of FIG. 24 in an expanded position with the introducer removed and with a collar disposed in position to retain the speculum in the expanded position. FIG. 26 depicts an interior view of the expanded speculum of FIGS. 25A to 25G disposed in a vagina. As shown in FIG. 26, the cervix C and vaginal walls V can be seen through the speculum 2200 and collar 2250 when disposed in the expanded and/or locked position. FIG. 27 depicts a sectional view of the expanded speculum of FIG. 25 disposed in a vagina showing additional structures of bladder and colon and anatomical location of the speculum.

In one exemplary method of insertion, the speculum 2200 and introducer 2100 are coupled together to collapse or expand the speculum 2200. In one exemplary aspect, the speculum and be placed onto an introducer during manufacturer. For example, if the flute/speculum is placed on an introducer during manufacture, the joint connections of both the posterior and the anterior arms of the flute, which maintain the support rods are settled along the introducer at the pedal points. The posterior arm of speculum slide onto the saddle/landing on the posterior side of the introducer until snug. Traction/pulling back in the distal direction on the arm of the anterior speculum with a support rod allows for the notch in this arm to be settled on the anterior prong of introducer. This closes the speculum along the introducer both anterior and posterior. Similarly, traction on the bilateral side arms of speculum again in the distal direction allow them to be attached on the introducer where the side prongs of introducer and the notches of the side arms meet will hold the device in the closed position. In this exemplary arrangement, the speculum in the closed position then has a grip at the distal end of introducer which helps guide the proximal end of closed speculum into a vagina in an upward or inward direction. The insertion continues generally until the introitus pads on flute are at the opening of vagina.

The provider (or patient optionally) then gently presses these pads together from the sides and lifts the anterior speculum arm off the prong freeing it from collapsed position anteriorly. Then each side arm of speculum is gently pressed out and off of the side prongs of introducer. Introducer is then grasped at grip location and pulled back/away from patient and removed from saddle. The introducer is no longer needed for duration of exam and can be discarded appropriately. The speculum then naturally expands out. If equipped or otherwise elected, the collar can be swiveled, hinged, or otherwise disposed into the position shown in FIGS. 25, 26, 27, 28A, 28E, and 28F to be placed along prong and notch locations described and shown herein. After the exam, the collar is removed from speculum arms and then rotated, hinged, or otherwise removed in a reverse manner from insertion. The patient or provider can gently pinch introitus pads in at side arms and then retract speculum out for removal. The speculum, introducer, and other materials are generally discarded appropriately or can be cleansed or otherwise sterilized for reuse if appropriate.

FIG. 28A to 28F depict aspects of an exemplary light 2800 that can be used in conjunction with an exemplary speculum 2900 or other speculum/flute detailed in this disclosure and with the exemplary collar 2950 or other collar detailed in this disclosure. The exemplary speculum 2900 holds the shape and integrity for vaginal wall retraction when in open position to allow for visualization of the vagina and cervix and exemplary collar 2950 that is shown as a round or semi-round piece that may or may not be attached to the speculum/flute. If attached, the collar 2950 has the ability to rotate on its axis/attachment location to swivel into a position where it can be additionally attached to the remaining speculum extensions/arms after the introducer/inserter is removed. The collar 2950 helps provide additional support and structure to the round spines of the speculum to maintain vaginal wall retraction and visualization of the anatomy.

The exemplary light 2800 is generally configured of a similar shape to collar 2950 and can be attached thereto either when the exemplary collar 2950 is disposed in the collapsed or expanded positions. The light 2800 includes a light structure 2808 and can include tabs or grasps 2802 and 2804 that extend off the light structure 2808 to allow the light 2800 to rest upon, hang, cling, or be affixed to the speculum, the collar, or the speculum and collar when connected as a unit. The grasps 2802 and 2804 can be formed solitary or can be disposed in multiple locations about the light 2800. The light 2800 includes a light computer 2806 provides technical informatics for light functioning on the light structure. The light computer 2806 can be disposed anywhere along the light structure 2808 and, optionally, can include a battery compartment or other power supply. Further, the light computer 2806 can include a switch 2814 provided to turn the light on/off. The switch 2814 can be a single switch or could be multiple switches and can provide options, such as to allow for color changes (e.g., white, green, yellow, etc.) and can allow for various levels of brightness. The structure 2808 is generally a case or covering that provides shape and support to the light components, such as wiring, battery, bulbs, etc. The structure 2808 maintains form and can be flat or rounded, partially circular, or entirely circular in form. The structure 2808 can provide a light charging location, optionally, as shown at 2812, which can be singular or provided in multiple locations along the structure 2808. The light charging location 2812 supports charging the light 2800 and allows for electrical charge of the lighting unit.

The light 2800 can include one or more lights 2810, which can be light-emitting diodes (LEDs), incandescent, ultraviolet, or other type of light. The lights 2810 can be singular or provided in multiple locations along or within the light structure 2808. The lights 2810 can be provided in various colors, such as, for example, white, yellow, orange, green, purple, red, blue, or other colors, can be provided with a filter or filters, and can be provided to rotate through various colors as desired. The lights 2810 can be situated to allow for light to be cast out of the structure 2808 and, when connected to a speculum/collar, will cast light through the lumen or down the arms of the speculum structure for improved visualization through the speculum and/or collar, in a vagina, or the surrounds thereof. Further, the lights 2810 can be arranged to increase or decrease in illumination as the examination proceeds. Even further, the lights 2810 can strobe, flash, or otherwise be provided to illuminate various or specific portions of the speculum, especially when the speculum is disposed in the expanded configuration. Even further still, the light 2800 can be removed from the speculum before being collapsed or can be arranged to remain attached to the collar 2950 and hinged or otherwise removed from the locked position before the speculum is collapsed for removal from a vagina.

The speculum(s) detailed herein can include a light source that is either integral, an attachment, an additional piece, or otherwise functional to provide light inside the elements of the speculum, including the rings, along the speculum, adjacent the speculum, or cast into the vagina via or in operation with the speculum. The light source can be filtered, bright, soft, or provided in different colors. For example, the light can be a green filtered light, a blue light, a yellow light, a white light, or combinations of these or other colors. Further, the light can travel along and inside the elements of the speculum(s) and can illuminate a region within the speculum, adjacent the speculum, proximate an opening of the vagina, or distal the opening of the vagina. Further still, the light source can be an LED, infrared, ultraviolet light, or other type of light.

Although the methods and apparatuses are described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus, the breadth and scope of the claimed disclosure should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. Any use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein can be described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

Although the preceding description contains significant detail in relation to certain preferred embodiments, it should not be construed as limiting the scope of the disclosure but rather as providing illustrations of the preferred embodiments.

Embodiments of the present disclosure encompass kits having one or more components of a system as disclosed herein. In some embodiments, the kit includes one or more system components, along with instructions for using the component(s) for example according to any of the methods disclosed herein.

All features of the described systems and devices described herein can be applicable to the described methods mutatis mutandis, and vice versa.

In addition, each reference provided herein is incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

While preferred embodiments of the present disclosure have been shown and described herein, it will be understood to those skilled in the art that such embodiments are provided by way of example only. Numerous variations, changes, and substitutions will now occur to those skilled in the art without departing from embodiments of the present disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A system for dilating a vagina of a patient during a pelvic exam, comprising:

a flute having a first retracting rod, a second retracting rod, a first nesting rod, a second nesting rod, a proximal foldable ring, and a distal foldable ring;

a handle having a first proximal coupling mechanism configured to releasably couple with the first retracting rod, a second proximal coupling mechanism configured to releasably couple with the second retracting rod, a first groove configured to at least partially receive the first nesting rod, a second groove configured to at least partially receive the second nesting rod, a first gripping mechanism and a second gripping mechanism operable to engage the flute when the proximal and distal foldable rings are in a folded orientation; and a ring collar, wherein the flute is configured to transition between an expanded state where the proximal and distal foldable rings are in an unfolded orientation and a collapsed state where the proximal and distal foldable rings are in the folded orientation, wherein the handle is configured to maintain the flute in the collapsed state when the first proximal coupling mechanism is coupled with the first retracting rod, the second proximal coupling mechanism is coupled with the second retracting rod, and the first and second gripping mechanisms are engaged with the flute, and wherein the ring collar is configured to engage the flute when the flute is in the expanded state.

2. The system according to claim 1, wherein the first proximal coupling mechanism comprises a first proximal extrusion, the second proximal coupling mechanism comprises a second proximal extrusion, the first retracting rod comprises a first slot configured to engage the first proximal extrusion, and the second retracting rod comprises a second slot configured to engage the second proximal extrusion.

3. The system according to claim 1, wherein the first gripping mechanism comprises a first external gripping mechanism having a first distal barb configured to engage a first narrow portion of the distal foldable ring, a second distal barb configured to engage a second narrow portion of the distal foldable ring, a first proximal barb configured to engage a first narrow portion of the proximal foldable ring, and a second proximal barb configured to engage a second narrow portion of the proximal foldable ring.

4. The system according to claim 1, wherein the second gripping mechanism comprises a second external gripping mechanism having a first distal barb configured to engage a third narrow portion of the distal foldable ring, a second distal barb configured to engage a fourth narrow portion of the distal foldable ring, a first proximal barb configured to engage a third narrow portion of the proximal foldable ring, and a second proximal barb configured to engage a fourth narrow portion of the proximal foldable ring.

5. The system according to claim 1, wherein the first gripping mechanism comprises a first internal gripping mechanism configured to engage the first nesting rod and a second internal gripping mechanism configured to engage the second nesting rod.

6. The system according to claim 5, wherein the handle comprises a slider mechanism operable to disengage the first proximal coupling mechanism from the first retracting rod and the second proximal coupling mechanism from the second retracting rod.

7. The system according to claim 1, wherein the distal foldable ring is engaged with the first retracting rod at a first engagement point, with the second retracting rod at a second engagement point, with the first nesting rod at a third engagement point, and with the second nesting rod at a fourth engagement point, and wherein the first engagement point is disposed 180° opposite that of the second engagement point and the third engagement point is disposed 180° opposite that of the fourth engagement point.

8. The system according to claim 1, wherein the first retracting rod comprises a first proximal prong, the second retracting rod comprises a second proximal prong, the first nesting rod comprises a third proximal prong, and the second nesting rod comprises a fourth proximal prong, and wherein the first and second proximal prongs are disposed proximal to the third and fourth proximal prongs when the flute is in the collapsed state.

9. The system according to claim 1, wherein the first retracting rod comprises a first proximal prong, the second retracting rod comprises a second proximal prong, the first nesting rod comprises a third proximal prong, and the second nesting rod comprises a fourth proximal prong, and wherein the ring collar comprises a first tab configured to engage a first slot of the first proximal prong, a second tab configured to engage a second slot of the second proximal prong, a third tab configured to engage a third slot of the third proximal prong, and a fourth tab configured to engage a fourth slot of the fourth proximal prong.

10. The system according to claim 1, wherein the ring collar comprises a light source.

11. The system according to claim 1, wherein the flute comprises at least one padding mechanism configured to engage an introitus of the patient.

12. A method of dilating a vagina of a patient during a pelvic exam by a gynecologist, the method comprising:

engaging a handle with a flute when the flute is in an expanded state, wherein the flute comprises a first retracting rod, a second retracting rod, a first nesting rod, a second nesting rod, a proximal foldable ring, and a distal foldable ring, and wherein the handle comprises a first proximal coupling mechanism configured to releasably couple with the first retracting rod, a second proximal coupling mechanism configured to releasably couple with the second retracting rod, a first groove configured to at least partially receive the first nesting rod, a second groove configured to at least partially receive the second nesting rod, a first gripping mechanism and a second gripping mechanism operable to engage the flute when the proximal and distal foldable rings are in a folded orientation;

transitioning the flute from the expanded state to a collapsed state;

inserting the flute at least partially within the vagina of the patient while the flute is in the collapsed state;

transitioning the flute from the collapsed state to the expanded state by disengaging the handle from the flute; and coupling a ring collar with the flute, wherein the ring collar operates to maintain the flute in the expanded orientation.

13. The method according to claim 12, wherein the flute is configured to transition between the expanded state where the proximal and distal foldable rings are in an unfolded orientation and the collapsed state where the proximal and distal foldable rings are in a folded orientation, wherein the handle is configured to maintain the flute in the collapsed state when the first proximal coupling mechanism is coupled with the first retracting rod, the second proximal coupling mechanism is coupled with the second retracting rod, and the first and second gripping mechanisms are engaged with the flute, and wherein the ring collar is configured to engage the flute via the first and second retracting rods and the first and second nesting rods of the flute.

14. The method according to claim 12, wherein the first proximal coupling mechanism comprises a first proximal extrusion, the second proximal coupling mechanism comprises a second proximal extrusion, the first retracting rod comprises a first slot configured to engage the first proximal extrusion, and the second retracting rod comprises a second slot configured to engage the second proximal extrusion.

15. The method according to claim 12, wherein the first gripping mechanism comprises a first external gripping mechanism having a first distal barb configured to engage a first narrow portion of the distal foldable ring, a second distal barb configured to engage a second narrow portion of the distal foldable ring, a first proximal barb configured to engage a first narrow portion of the proximal foldable ring, and a second proximal barb configured to engage a second narrow portion of the proximal foldable ring.

16. The method according to claim 12, wherein the second gripping mechanism comprises a second external gripping mechanism having a first distal barb configured to engage a third narrow portion of the distal foldable ring, a second distal barb configured to engage a fourth narrow portion of the distal foldable ring, a first proximal barb configured to engage a third narrow portion of the proximal foldable ring, and a second proximal barb configured to engage a fourth narrow portion of the proximal foldable ring.

17. The method according to claim 12, wherein the first gripping mechanism comprises a first internal gripping mechanism configured to engage the first nesting rod and a second internal gripping mechanism configured to engage the second nesting rod.

18. The method according to claim 17, wherein the handle comprises a slider mechanism operable to disengage the first proximal coupling mechanism from the first retracting rod and the second proximal coupling mechanism from the second retracting rod.

19. The method according to claim 12, wherein the distal foldable ring is engaged with the first retracting rod at a first engagement point, with the second retracting rod at a second engagement point, with the first nesting rod at a third engagement point, and with the second nesting rod at a fourth engagement point, and wherein the first engagement point is disposed 180° opposite that of the second engagement point and the third engagement point is disposed 180° opposite that of the fourth engagement point.

20. The method according to claim 12, wherein the first retracting rod comprises a first proximal prong, the second retracting rod comprises a second proximal prong, the first nesting rod comprises a third proximal prong, and the second nesting rod comprises a fourth proximal prong, and wherein the first and second proximal prongs are disposed proximal to the third and fourth proximal prongs when the flute is in the collapsed state.

21. The method according to claim 12, wherein the first retracting rod comprises a first proximal prong, the second retracting rod comprises a second proximal prong, the first nesting rod comprises a third proximal prong, and the second nesting rod comprises a fourth proximal prong, and wherein the ring collar comprises a first tab configured to engage a first slot of the first proximal prong, a second tab configured to engage a second slot of the second proximal prong, a third tab configured to engage a third slot of the third proximal prong, and a fourth tab configured to engage a fourth slot of the fourth proximal prong.

22. The method according to claim 12, wherein the ring collar comprises a light source.

* * * * *